(12) United States Patent
Verkman et al.

US008394788B2

(10) Patent No.: US 8,394,788 B2
(45) Date of Patent: Mar. 12, 2013

(54) PHENYLSULFOXYOXAZOLE COMPOUND INHIBITORS OF UREA TRANSPORTERS

(75) Inventors: Alan S. Verkman, San Francisco, CA (US); Marc Harris Levin, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 388 days.

(21) Appl. No.: 12/515,000

(22) PCT Filed: Nov. 16, 2007

(86) PCT No.: PCT/US2007/085016
§ 371 (c)(1),
(2), (4) Date: Jan. 19, 2010

(87) PCT Pub. No.: WO2008/061248
PCT Pub. Date: May 22, 2008

(65) Prior Publication Data
US 2010/0305105 A1   Dec. 2, 2010

Related U.S. Application Data

(60) Provisional application No. 60/859,665, filed on Nov. 16, 2006, provisional application No. 60/859,800, filed on Nov. 16, 2006.

(51) Int. Cl.
*A01N 43/00* (2006.01)
*A01N 43/50* (2006.01)
*A01N 43/76* (2006.01)
*A61K 31/55* (2006.01)
*A61K 31/415* (2006.01)
*A61K 31/42* (2006.01)
*A61K 31/535* (2006.01)
*C12N 5/00* (2006.01)
*C12N 5/02* (2006.01)

(52) U.S. Cl. .................. 514/217.08; 435/375; 514/398; 514/376; 514/236.8

(58) Field of Classification Search .................. None
See application file for complete search history.

(56) References Cited

U.S. PATENT DOCUMENTS

| 5,441,875 A | 8/1995 | Hediger ........................ 435/69.1 |
| 6,441,013 B1 | 8/2002 | Greiner et al. ................ 514/376 |
| 6,737,426 B1 | 5/2004 | Gericke et al. ........... 514/252.13 |
| 2010/0190796 A1 | 7/2010 | Verkman et al. .............. 514/248 |

FOREIGN PATENT DOCUMENTS

| WO | WO 02/100842 A1 | 12/2002 |
| WO | WO 2008/061247 | 5/2008 |
| WO | WO 2008/061248 | 5/2008 |
| WO | WO 2008/067196 | 6/2008 |

OTHER PUBLICATIONS

Babii et al., "Conversion of N-(1-Arylsulfonyl-2,2-dichloroethenyl)carboxamides into Derivatives of 4,5-Dimercaptooxazole," *Russian Journal of Organic Chemistry* 37(8):1149-1152, 2001.
Bagnasco et al., "Cloning and characterization of the human urea transporter UT-A1 and mapping of the human Slc14a2 gene," *American Journal of Physiology & Renal Physiology*, 281:F400-F406, 2001.
Bagnasco, "Gene structure of urea transporters," *American Journal of Physiology & Renal Physiology*, 284:F3-F10, 2003.
Bagnasco, "Role and regulation of urea transporters," *Pflügers Archive: European Journal of Physiology*, 450(4):217-226, 2005.
Cohn et al., "Extracellular lysines on the plasmodial surface anion channel involved in Na+ exclusion," *Molecular & Biochemical Parasitology*, 132:27-34, 2003.
Fenton et al., "Urinary concentrating defect in mice with selective deletion of phloretin-sensitive urea transporters in the renal collecting duct," *Proc. Natl. Acad. Sci. USA* 101(19):7469-7474, 2004.
Fenton et al., "Renal Phenotype of UT-A Urea Transporter Knockout Mice," *J. Am. Soc. Nephrol.* 16:1583-1592, 2005.
Fröhlich et al., "Urea transport in MDCK cells that are stably transfected with UT-A1," *American Journal of Physiology & Cell Physiology*, 286:C1264-C1270, 2004.
Fröhlich et al., "Regulation of UT-A1-mediated transepithelial urea flux in MDCK cells," *American Journal of Physiology & Cell Physiology*, 291:C600-C606, 2006.
Goldsmith, "Current Treatments and Novel Pharmacologic Treatments for Hyponatremia in Congestive Heart Failure," *The American Journal of Cardiology*, 95(9A):14B-23B, 2005.
Goodman, "Transport of small molecules across cell membranes: water channels and urea transporters," *Advances in Physiology Education*, 26(3):146-157, 2002.
Karakashian et al., "Cloning and Characterization of Two New Isoforms of the Rat Kidney Urea Transporter: UT-A3 and UT-A4," *Journal of the American Society of Nephrology*, 10:230-237, 1999.
Klein et al., "Upregulation of Urea Transporter UT-A2 and Water Channels AQP2 and AQP3 in Mice Lacking Urea Transporter UT-B," *Journal of the American Society of Nephrology*, 15:1161-1167, 2004.
Leroy et al., "Hyperosmotic NaCl and Urea Synergistically Regulate the Expression of the UT-A2 Urea Transporter in Vitro and in Vivo," *Biochemical and Biophysical Research Communications*, 271(2):368-373, 2000.
Levin et al., "Urearetics: a small molecule screen yields nanomolar potency inhibitors of urea transporter UT-B," *The FASEB Journal*, 21:551-536, 2007.

(Continued)

*Primary Examiner* — Jeffrey S Lundgren
*Assistant Examiner* — William Lee
(74) *Attorney, Agent, or Firm* — Seed IP Law Group PLLC

(57) ABSTRACT

Provided herein are small molecule compounds that alter the transport activity of solute transporters, particularly urea transporters. The compounds described herein belong to the phenylsulfoxyoxazole, phenylsulfoxyimidazole, phenylsulfoxythiazole class of compounds. The compounds described herein are useful for increasing solute clearance in states of fluid overload and for treating cardiovascular, renal, and metabolic diseases, disorders, and conditions. Methods for identifying and using these agents that inhibit urea transporters are described herein.

40 Claims, 7 Drawing Sheets

OTHER PUBLICATIONS

Lucien et al., "Characterization of the Gene Encoding the Human Kidd Blood Group/Urea Transporter Protein," *The Journal of Biological Chemistry*, 273(21):12973-12980, 1998.

Ma et al., "Severely Impaired Urinary Concentrating Ability in Transgenic Mice Lacking Aquaporin-1 Water Channels," *The Journal of Biological Chemistry*, 273(8):4296-4299, 1998.

Macey et al., "Independence of Water and Solute Pathways in Human RBCs," *Journal of Membrane Biology*, 134(3):241-250, 1993.

Martial et al., "Urea derivatives as tools for studying the urea-facilitated transport system," *Pflügers Archive: European Journal of Physiology*, 423:51-58, 1993.

Mayrand et al., "Urea and Ethylene Glycol-facilitated Transport Systems in the Human Red Cell Membrane," *The Journal of General Physiology*, 81:221-237, 1983.

Mazeron et al., "A Theoretical Approach of the Measurement of Osmotic Fragility of Erythrocytes by Optical Transmission," *Photochemistry and Photobiology*, 72(2):172-178, 2000.

Miller, "Hyponatremia and Arginine Vasopressin Dysregulation: Mechanisms, Clinical Consequences, and Management," *Journal of the American Geriatrics Society*, 54(2):345-353, 2006.

Moehlenbrock et al., "Use of microchip-based hydrodynamic focusing to measure the deformation-induced release of ATP from erythrocytes," *The Analyst*, 131:930-937, 2006.

Sands, "Regulation of Urea Transporter Proteins in Kidney and Liver," *The Mount Sinai Journal of Medicine*, 67(2):112-119, 2000.

Sands, "Mammalian Urea Transporters," *Annual Review of Physiology*, 65:543-566, 2003.

Sands, "Renal urea transporters," *Current Opinion in Nephrology and Hypertension*, 13(5):525-532, 2004.

Sands et al., "Urinary Concentrating Ability in Patients with Jk(a-b-) Blood Type Who Lack Carrier-Mediated Urea Transport," *Journal of the American Society of Nephrology* 2:1689-1696, 1992.

Sands et al., "Urea transporters in kidney and erythrocytes," *The American Journal of Physiology*, 273:F321-F339, 1997.

Shayakul et al., "The SLC14 gene family of urea transporters," *Pflügers Archive: European Journal of Physiology*, 447:603-609, 2004.

Sidoux-Walter et al., "At Physiological Expression Levels the Kidd Blood Group/Urea Transporter Protein Is Not a Water Channel," *The Journal of Biological Chemistry*, 274(42):30228-30235, 1999.

Tradtrantip et al., "Aquaporin water channels in transepithelial fluid transport," *The Journal of Medical Investigation*, 56:179-184, 2009.

Tsukaguchi et al., "Cloning and Characterization of the Urea Transporter UT3," *The Journal of Clinical Investigation*, 99(7):1506-1515, 1997.

Verkman, "Physiological importance of aquaporins: lessons from knockout mice," *Current Opinion in Nephrology and Hypertension*, 9(5):517-522, 2000.

Verkman, "Roles of Aquaporins in Kidney revealed by Transgenic Mice," *Seminars in Nephrology*, 26:200-208, 2006.

Xiuli et al., "Glucose Transporter 1, Distribution in the Brain and in Neural Disorders: Its Relationship With Transport of Neuroactive Drugs Through the Blood-Brain Barrier," *Biochemical Genetics*, 43(3/4):175-187, 2005.

Yang et al., "Urea Transporter UT3 Functions as an Efficient Water Channel," *The Journal of Biological Chemistry*, 273(16):9369-9372, 1998.

Yang et al., "Urea-selective Concentrating Defect in Transgenic Mice Lacking Urea Transporter UT-B," *The Journal of Biological Chemistry*, 277(12):10633-10637, 2002.

Yang et al., "Analysis of Double Knockout Mice lacking Aquaporin-1 and Urea Transporter UT-B," *The Journal of Biological Chemistry*, 277(39):36782-36786, 2002.

Zyabrev et al., "Synthesis of Derivatives of 5-Mercaptoimidazole From N-Arylsulfonylmethylimidoyl Isothiocyanates," *Russian Journal of Organic Chemistry* 30(5):715-719, 1994.

PHENYLSULFOXYOXAZOLE COMPOUND INHIBITORS OF UREA TRANSPORTERS

CROSS-REFERENCE TO RELATED APPLICATIONS

This application is a U.S. national stage application filed under 35 U.S.C. §371 of International Patent Application PCT/US2007/085016, accorded an international filing date of Nov. 16, 2007, which claims the benefit of U.S. Provisional Application No. 60/859,800 filed Nov. 16, 2006 and U.S. Provisional Application No. 60/859,665 filed Nov. 16, 2006, all of which are incorporated herein by reference in their entirety.

STATEMENT OF GOVERNMENT INTEREST

This invention was made with government support under Grant No. DK35124 awarded by National Institutes of Health. The government has certain rights in this invention.

BACKGROUND OF THE INVENTION

1. Field of the Invention

Agents that alter the transport activity of small, neutrally charged solutes by solute transporters are needed as therapeutic agents for increasing solute clearance in states of fluid overload and for treating diseases and conditions such as hypertension. Methods for identifying and using agents that inhibit solute transporters such as urea transporters are described herein.

2. Description of the Related Art

Urea is generated as the major end product of hepatic nitrogen metabolism and is excreted primarily by the kidney. Urea and sodium chloride are the major solutes in the hyperosmolar renal medulla. In the antidiuretic kidney, urea is greatly concentrated with respect to plasma (up to 100 times in humans and 250 times in rodents) by countercurrent multiplication and exchange mechanisms (Bankir et al., In The Kidney (6th Edition), pages 637-679, Brenner, B M, ed., (WB Saunders Company, Philadelphia, Pa.) (2000)). Of central importance to these mechanisms is intrarenal urea recycling, which requires facilitated urea transport by molecular urea transporters (UTs). UTs are comprised of two major subfamilies encoded by different genes (UT-A and UT-B) (see, e.g., Bagnasco, Am. J. Physiol. 284:F3-F10 (2003); Shayakul et al., Pflügers Arch. 447:603-609 (2004); Yang et al., J. Biol. Chem. 273:9369-72 (1998)). In kidney, a single UT-B isoform is expressed in vasa recta while several splice variant UT-A-type transporters are expressed in kidney tubule epithelia (see, e.g., Sands, Curr. Opin. Nephrol. Hypertens. 13:525-32 (2004)).

Phenotype analysis of mice separately lacking vasa recta UT-B or inner medullary collecting duct UT-A1/3 implicated UT involvement in the formation of concentrated urine and in renal urea clearance (see, e.g., Yang et al., J. Biol. Chem. 277:10633-37 (2002); Fenton et al., Proc. Natl. Acad. Sci. USA 101:7469-74 (2004); Fenton et al., J. Am. Soc. Nephrol. 16, 1583-92 (2005)). The UT-B knock-out mice that were generated manifested a urea-selective urinary concentrating defect associated with urinary hypoosmolality and increased renal urea clearance (Yang et al., supra). UT-B is also expressed outside of the kidney, most notably and in highest abundance in red blood cell (RBC) membranes. Loss-of-function human UT-B mutations result in greatly reduced urea permeability in RBC and a mild urinary concentrating defect (Sands et al., J. Am. Soc. Nephrol. 2:1689-96 (1992); Lucien et al., J. Biol. Chem. 273:12973-80 (1998)).

Diuretics are administered widely in humans to increase renal salt and water clearance in a variety of conditions that are associated with total body fluid overload, such as congestive heart failure and cirrhosis, as well in normovolemic states such as hypertension and syndrome of inappropriate secretion of antidiuretic hormone (SIADH). Most diuretics are inhibitors of salt absorption by kidney tubules, such as a furosemide block of $Na^+/K^+/2Cl^-$ co-transport in the thick ascending limb of Henle and a thiazide block of $Na^+/Cl^-$ co-transport in the distal tubule. Recently, a new type of diuretic, called an "aquaretic," has been developed to increase renal water clearance in hyponatremia associated with fluid overload or SIADH (see, e.g., Goldsmith, Am. J. Cardiol. 95:14B-23B (2005); Miller, J. Am. Geriatr. Soc. 54:345-53 (2006)). Vasopressin-2 receptor (V2R) antagonist aquaretics have been approved for clinical use in some countries, though not yet in the United States, and aquaporin inhibitor aquaretics are under development.

Functional studies in knock-out mice indicate a critical role for urea transporters (UTs) in the urinary concentrating mechanism and in renal urea clearance. However, potent and specific urea transport blockers have not been available. Accordingly, a third type of diuretic is needed: one that targets renal urea clearance mechanisms. Because urea is of at least equal importance to NaCl in the renal countercurrent mechanism for urinary concentration (see, e.g., Bankir et al., supra; Masilamani et al., In The Kidney (6th Edition), Brenner, ed. Philadelphia, Pa.; WB Saunders Company; pages 595-35; (2000)), such diuretics are needed for increasing solute clearance in states of fluid overload, hypertension, and may also be useful in prolonging dialysis-free survival in chronic renal insufficiency. A need also exists for methods for rapid screening of compounds to identify potential urea transporter inhibitors and other compounds that effectively increase renal water and solute clearance for subjects who are exhibiting a water-retaining state.

BRIEF SUMMARY OF THE INVENTION

Briefly stated, the present invention is directed to compounds, compositions, and methods for treatment of one or more diseases associated with aberrant transport of a neutrally charged solute across a cell membrane by a cell transporter. Such methods include administration to a subject or biological source as provided herein, such as a human or other warm-blooded animal in need thereof, an effective amount of at least one compound described herein. In particular, described herein are inhibitors of urea transporters. In one embodiment, a composition is provided comprising a pharmaceutically acceptable excipient and a compound having a structure of formula (I). In other specific embodiments, compositions are provided comprising a pharmaceutically acceptable excipient and a compound having any one of the substructures of formulae (Ia-Ij) as described in detail herein.

In one embodiment, the compound has the following structure (I):

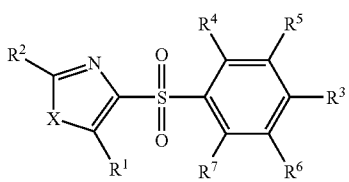

or a pharmaceutically acceptable salt, prodrug or stereoisomer thereof, comprising substituents as described in detail herein.

In a more specific embodiment of structure (I), X is O and the compound, or a pharmaceutically acceptable salt, prodrug or stereoisomer thereof, has substituents as described in greater detail herein.

In another more specific embodiment of structure (I), X is NH and the compound, or a pharmaceutically acceptable salt, prodrug or stereoisomer thereof, has substituents as described in greater detail herein.

In yet another more specific embodiment of structure (I), X is S and the compound, or a pharmaceutically acceptable salt, prodrug or stereoisomer thereof, has substituents as described in greater detail herein.

The phenylsulfoxyoxazole (also spelled phenylsulfoxyoxozole), phenylsulfoxyimidazole, and phenylsulfoxythiozole compounds having the structure (I) and substructures (including substructures of formulae (Ia-Ij)) described herein may be used to alter (i.e., increase or decrease in a statistically significant or biologically significant manner) transport activity of urea by at least one urea transporter. In particular embodiments, the transporter activity of a urea transporter is inhibited, thus the compounds are capable of preventing, blocking, or decreasing transport of urea across a cell membrane. In one embodiment, at least one compound of structure (I) described herein inhibits transport of urea by a UT-B transporter. In another embodiment, at least one of structure (I) described herein inhibits the capability of a UT-A transporter to transport urea. In particular embodiments, the UT-A transporter is at least one of UT-A1, UT-A2, UT-A3, UT-A4, and UT-A5. In certain embodiments, the cell is a renal cell, a brain cell, a red blood cell, or a testis cell. In a particular embodiment, the cell is a renal cell. In another particular embodiment, the cell is a red blood cell wherein the red blood cell comprises at least a UT-B transporter.

In other embodiments, methods are provided for inhibiting transport of urea across a cell membrane comprising contacting a cell with a composition that comprises at least one of the compounds of structure (I) (including substructures of formulae (Ia-Ij)) described herein, wherein the cell comprises at least one urea transporter. In one embodiment, at least one compound described herein inhibits the capability of a UT-B transporter to transport urea. In another embodiment, the at least one phenylsulfoxyoxazole, phenylsulfoxyimidaozole, or phenylsulfoxythiozole compound inhibits the capability of a UT-A transporter to transport urea. In particular embodiments, the UT-A transporter is at least one of UT-A1, UT-A2, UT-A3, UT-A4, and UT-A5. In certain embodiments, the cell is a renal cell, a brain cell, a red blood cell, or a testis cell. In a particular embodiment, the cell is a renal cell. In another particular embodiment, the cell is a red blood cell and the red blood cell comprises at least a UT-B transporter.

Also provided herein is a method of treating a disease or disorder or condition comprising administering to a subject in need thereof, the composition comprising at least one phenylsulfoxyoxazole, phenylsulfoxyimidazole, or phenylsulfoxythiozole compound described herein. The disease, disorder, or condition that may be treated includes a cardiovascular disease, syndrome of inappropriate antidiuretic hormone secretion (SIADH), cirrhosis, azotemia, acute renal failure, chronic renal insufficiency, fluid retention, and abnormal uresis. In certain particular embodiments, the cardiovascular disease is congestive heart failure or hypertension.

In one embodiment, a method is provided for treating a disease or disorder or condition associated with aberrant transport of a neutrally charged solute in a subject by administering to the subject a composition comprising a physiologically acceptable excipient and at least one compound of structure (I) or any substructure (including substructures of formulae (Ia-Ij)) described above and in further detail herein. In a specific embodiment, the disease, disorder, or condition is associated with a fluid retention imbalance; in another certain specific embodiment, the fluid retention imbalance comprises urea clearance insufficiency. In other particular embodiments, the disease, disorder, or condition is selected from a cardiovascular disease, syndrome of inappropriate antidiuretic hormone secretion (SIADH), cirrhosis, azotemia, acute renal failure, chronic renal insufficiency, fluid retention, and abnormal uresis. In particular embodiments, the cardiovascular disease, disorder, or condition is selected from hypertension and congestive heart failure. In a particular embodiment, urea clearance insufficiency is renal urea clearance insufficiency. In one embodiment, the neutrally charged solute is urea. In still another embodiment, treating the disease, disorder, or condition comprises inhibiting the capability of at least one urea transporter to transport urea. In certain specific embodiments, the at least one urea transporter is a UT-B transporter. In other certain specific embodiments, the at least one urea transporter is a UT-A transporter selected from UT-A1, UT-A2, UT-A3, UT-A4, and UT-A5.

In another embodiment, a method of altering transport of urea across a cell membrane by a urea transporter in a cell is provided in which the method comprises contacting (a) the cell with (b) a composition comprising a physiologically acceptable excipient and at least one compound of structure (I) or any substructure (including substructures of formulae (Ia-Ij)) described above and in further detail herein. In certain specific embodiments, the at least one urea transporter is a UT-B transporter. In other certain specific embodiments, the at least one urea transporter is a UT-A transporter selected from UT-A1, UT-A2, UT-A3, UT-A4, and UT-A5. In other specific embodiments the cell is a renal cell, a brain cell, a red blood cell, or a testis cell. In other specific embodiments the cell is a renal cell, a brain cell, a red blood cell, or a testis cell.

Also provided herein is a method of treating a disease, disorder, or condition comprising administering to a subject in need thereof, the composition comprising a physiologically acceptable excipient and at least one compound of structure (I) or any substructure (including substructures of formulae (Ia-Ij)) described above and in further detail herein. The disease, disorder, or condition that may be treated includes a cardiovascular disease, syndrome of inappropriate antidiuretic hormone secretion (SIADH), cirrhosis, azotemia, acute renal failure, chronic renal insufficiency, fluid retention, and abnormal uresis. In a particular embodiment, the cardiovascular disease is congestive heart failure or hypertension.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells and equivalents thereof known to those skilled in the art, and so forth. The term "about" when referring to a number or a numerical range means that the number of numerical range referred to is an approximation within experimental variability (or statistically, experimental error), and thus the number or numerical range may vary between 1% and 15% of the stated number of numerical range. The term "comprising" (and related terms such as "comprise" or "comprises" or "having" or "including") is not intended to exclude that in other certain embodiments, for example, an embodiment of any composition of matter, composition, method, or process, or the like, described herein may "consist of" or "consist essentially of" the described features.

All U.S. patents, U.S. patent application publications, U.S. patent applications, foreign patents, foreign patent applications, and non-patent publications referred to in this specification and/or listed in the Application Data Sheet, are each incorporated herein by reference, in their entirety.

BRIEF DESCRIPTION OF THE DRAWINGS

FIG. 2(A) demonstrate the effect of acetamide concentration on RBC osmotic lysis. Human RBC suspensions, loaded with indicated concentrations of acetamide, were diluted in acetamide-free buffer in the absence (open circles) or presence of 0.7 mM phloretin (closed circles). RBC lysis was assayed by absorbance at 710 nm (O.D.$_{710}$) (±SE, 4 wells per condition). The dashed line indicates the conditions chosen for high-throughput screening. FIG. 2(B) presents a frequency histogram of O.D.$_{710}$ values for positive and negative controls from eight 96-well plates, with z'-value shown.

FIG. 6a illustrates concentration-inhibition curves for indicated compounds (structures shown in FIG. 5A) determined by light scattering in response to a 100-mM inwardly directed urea gradient. RBCs were incubated for 5 minutes with compounds at indicated concentrations prior to stopped-flow measurements. FIG. 6B shows numerically simulated inhibitor concentration-dependence used to determine EC$_{50}$ from stopped-flow experiments as in FIG. 6A. The inverse of normalized cell volume, V$_o$/V(t), is plotted to approximate the light-scattering data at the indicated percentages of urea transport inhibition. FIG. 6C illustrates the membrane sidedness of UT-B inhibition. Experiments were performed as described for FIG. 6A and in the Examples, except that inhibitors (0.1 μM urea$_{inh}$-101 and 0.05-0.2 μM urea$_{inh}$-302) added only to the urea-containing solution (250 mM urea+PBS) where indicated. FIG. 6D illustrates the reversibility of UT-B inhibition. Where indicated, inhibitors (0.1 μM urea$_{inh}$-101 and 0.4 μM urea$_{inh}$-302) were washed out following a 10 min incubation, prior to stopped-flow measurements.

FIG. 7A illustrates dose-inhibition relationships for urea$_{inh}$-101 (left) and urea$_{inh}$-302 (right) against mouse UT-B determined by stopped-flow light scattering measurements performed using wild-type mouse RBCs in response to a 100-mM inwardly directed gradient of N-methylurea. FIG. 7B shows UT-A1-mediated urea flux in stably transfected MDCK cells. Cells were treated (open circles and open triangles) or not treated (closed circles) with 10 μM forskolin. Where indicated, phloretin (0.7 mM) was present (open triangles) (±SE, 3 filters per condition). The dashed line indicates the time chosen (15 min) to evaluate UT-A1 inhibition as shown in FIG. 7C. FIG. 7C illustrates concentration-dependent inhibition of mouse UT-B (triangles) and rat UT-A1 (circles) by urea$_{inh}$-101 (closed symbols) and urea$_{inh}$-302 (open symbols), determined from data obtained from experiments as in FIGS. 7A and 7B.

FIG. 8A presents representative traces of mouse RBC water permeability performed at 10° C., with genotypes and conditions indicated. Inhibitors ureainh-201 and urea$_{inh}$-302 were used at 25 μM. FIG. 8B presents osmotic water permeability coefficients (P$_f$) from experiments as illustrated in FIG. 8A (±SE, 3-7 curves per group of RBCs pooled from 4 mice per genotype). *, P<0.01 compared with no inhibitor; #, P<0.01 compared with wild-type (no inhibitor).

DETAILED DESCRIPTION OF THE INVENTION

Figure 1:
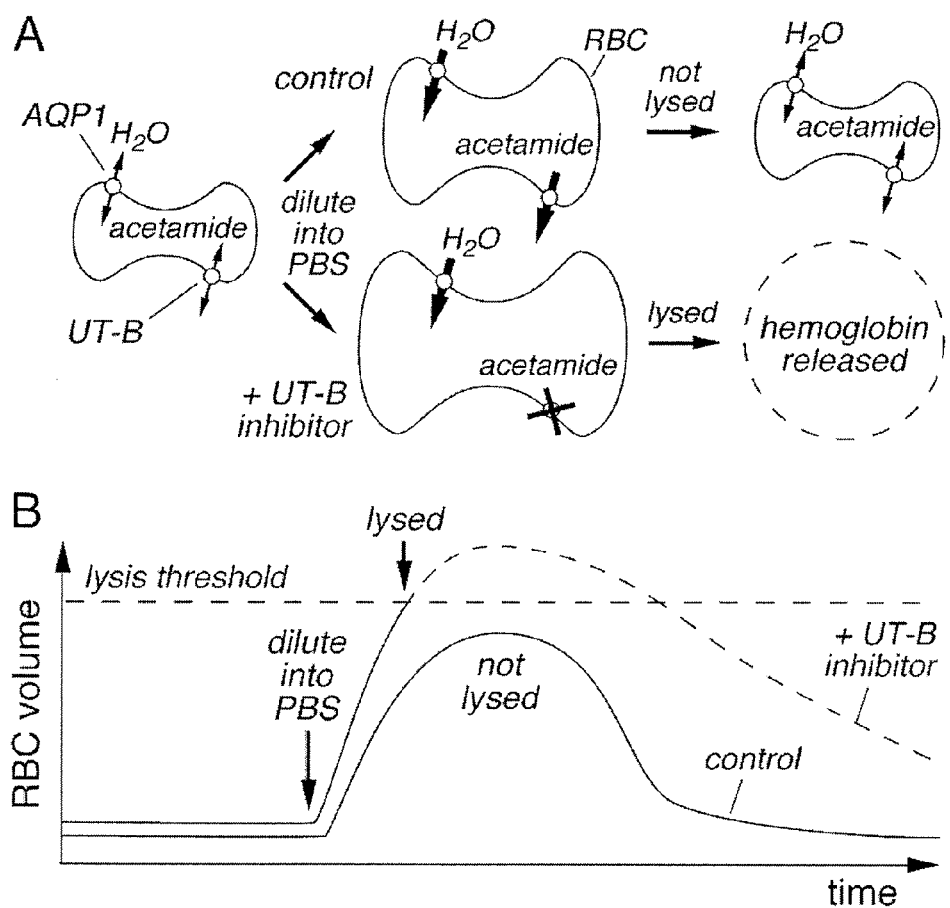
FIGS. 1A and 1B illustrate an erythrocyte osmotic lysis assay for identifying inhibitors of urea transporters. (A) The schematic represents human RBCs that express water and urea channels (AQP1 and UT-B, respectively) and that are preloaded with urea or a urea analog, such as acetamide. Following replacement of the external hyperosmolar buffer with an urea/acetamide-free isosmolar solution, water entry results in cell swelling, which is limited by UT-B-mediated urea/acetamide efflux. Under optimized assay conditions, UT-B-facilitated urea/acetamide transport prevents osmotic lysis (top), whereas UT-B inhibition impairs urea/acetamide exit resulting in substantial lysis (bottom). (B) The graph illustrates biphasic cell volume changes in the lysis assay. Increased RBC volume beyond a threshold results in lysis. The dashed curve shows the hypothetical time course of RBC volume if lysis had not occurred.

As stated above, the present invention is directed to compounds, compositions, and methods for treatment of one or more diseases associated with or related to aberrant transport of a neutrally charged solute across a cell membrane by a cell transporter. Aberrant transport of a neutrally charged solute (e.g., urea) may be associated with a fluid retention imbalance, such as urea clearance insufficiency. Potent, specific, small molecule inhibitors of urea transporters (UTs) are described herein that may be used to treat diseases, disorders, or conditions including but not limited to hypertension, congestive heart failure, syndrome of inappropriate antidiuretic hormone secretion (SIADH), cirrhosis, azotemia, acute renal failure, chronic renal insufficiency, fluid retention, and abnormal uresis.

Previously, the only available UT inhibitors included compounds that are nonspecific and exhibit moderate or low activity such as the non-specific membrane intercalating agent phloretin (exhibiting activity at >0.5 mM); urea analogs such as thiourea, methylurea, and dimethylurea (exhibiting activity at 50-100 mM); (see, e.g., Mayrand et al., supra), and chemically modified urea analogs (exhibiting irreversible activity at 30-100 μM) (Martial et al., *Pflügers Arch.* 423:51-58 (1993)). As described herein, a high-throughput screening method was developed and used to discover and characterize UT inhibitors that are drug-like small molecules with high chemical diversity and high affinity. Potent UT inhibitors, which include inhibitors of UT-B, were identified and belong to the phenylsulfoxyoxazole, phenylsulfoxyimidazole, and phenylsulfoxythiazole classes of compounds.

As described in greater detail herein, compositions used for treating a subject in need thereof also include physiologically or pharmaceutically acceptable (i.e., suitable) excipients that are appropriate for the delivery and stability of a compound. Small molecule compounds useful for treating such diseases and disorders belong to the phenylsulfoxyoxazole phenylsulfoxyimidazole, and phenylsulfoxythiazole classes of compounds and have the following structures (arbitrarily designated as "I") and substructures.

In one embodiment, the compound has the following structure (I):

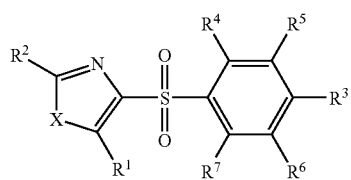

(I)

or a pharmaceutically acceptable salt, prodrug or stereoisomer thereof,
wherein
X is $NR^8$, O, or S;
$R^1$ is hydrogen, hydroxyl, halogen, alkyl, aryl, arylalkyl, arylalkylamino, sulfhydryl, thioalkyl, aminyl, amidyl, heterocycle, or heterocycloalkyl;
$R^2$ is hydrogen, hydroxyl, halogen, alkyl, aryl, arylalkyl, arylalkylamino, heterocycle or heterocycloalkyl;
$R^3$, $R^4$, $R^5$, $R^6$ and $R^7$ are each the same or different and independently hydrogen, halogen or alkyl; and
$R^8$ is hydrogen or alkyl.

In certain embodiments of structure (I), each of $R^4$, $R^5$, $R^6$, and $R^7$ is the same or different and independently hydrogen, or halogen, or $C_{1-6}$ alkyl. In particular embodiments of structure (I), at least two of $R^4$, $R^5$, $R^6$ and $R^7$ are hydrogen. In yet other particular embodiments of structure (I), each of $R^4$, $R^5$, $R^6$ and $R^7$ is hydrogen. In other embodiments of structure (I), x is O or NH.

In further embodiments of structure (I), $R^1$ is substituted or unsubstituted alkyl, sulfhydryl, thioalkyl, aminyl, amidyl, substituted or unsubstituted aryl, heterocycloalkyl containing at least N or O, arylalkylamino, or a heterocycle having at least N or O. In yet other embodiments of structure (I), $R^2$ is aryl, alkoxylaryl, or a 5-7-membered heterocycle containing at least O or S. In certain embodiments of structure (I), $R^2$ is unsubstituted phenyl or is phenyl substituted with halogen, $C_{1-6}$ alkyl, or $C_{1-6}$ alkoxy at a position meta or para to the linking carbon, that is, the carbon through which $R^2$ is linked to the rest of the structure. In more particular embodiments of structure (I), $R^2$ is unsubstituted phenyl; phenyl mono-substituted with fluoro, chloro, methyl, or methoxy at a position meta or para to the linking carbon; thiophene-2-yl; or furan-2-yl.

In further embodiments of structure (I), $R^3$ is hydrogen, halogen, or $C_{1-6}$ alkyl. In more particular embodiments, $R^3$ is hydrogen, halogen, or methyl. In other more particular embodiments, X is O. In some embodiments of structure (I), $R^1$ is —$S(CH_2)_nC(=O)NHR^{10}$ wherein n is 1 to 6 and $R^{10}$ is hydrogen, straight-chain $C_{1-6}$ alkyl, arylalkyl, or heterocycloalkyl. In other embodiments of structure (I), $R^1$ is —$N(R^{11})(R^{12})$ wherein $R^{11}$) and $R^{12}$ are the same or different and are selected from hydrogen, $C_{1-6}$ alkyl, or arylalkyl. In yet further embodiments of structure (I), $R^1$ is a heterocycle having at least N; —S-benzothioate; or —$SR^{13}$ wherein $R^{13}$ is hydrogen or $C_{1-6}$ alkyl. In certain other particular embodiments of structure (I), $R^1$ is —S-(2-mercaptoacetamidyl); —N-benzylamino; —S—[N-(furan-2-yl-methyl)-2-mercaptoacetamidyl); —N-dimethylamino; —N-morpholino; —N-hexahydro-1-H-azepinyl; —S-mercaptomethyl; sulfhydryl; or —S-benzothioate.

In certain embodiments of structure (I), when X is O, $R^1$ is —S-(2-mercaptoacetamidyl) and the compound has a substructure of the following formula (Ia):

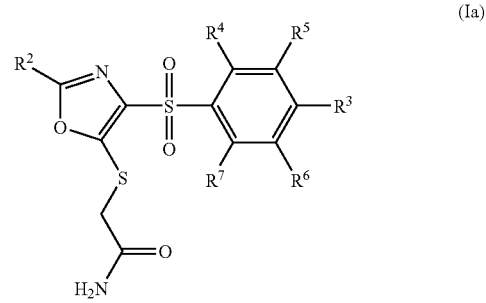

(Ia)

or pharmaceutically acceptable salts, prodrugs or stereoisomers thereof.

In a certain embodiment, when the compound has substructure Ia, $R^2$ is unsubstituted aryl; mono-substituted aryl wherein the substituent is meta or para to the linking carbon; or substituted or unsubstituted heterocycle. In some embodiments, $R^2$ is unsubstituted phenyl; mono-substituted phenyl wherein the substituent is meta or para to the linking carbon and is halogen, $C_{1-6}$ alkyl, or $C_{1-6}$ alkoxy; or a five- or six-member heteroaryl having at least O or S. In certain particular embodiments, $R^2$ is unsubstituted phenyl; mono-substituted phenyl with fluoro, chloro, or methyl, at a position meta or para to the linking carbon; thiophene-2-yl; or furan-2-yl.

In some embodiments, when the compound has substructure Ia, $R^3$ is hydrogen, halogen, or $C_{1-6}$ alkyl. In more particular embodiments, $R^3$ is hydrogen, halogen, or methyl. In certain embodiments, when the compound has substructure Ia, each of $R^4$, $R^5$, $R^6$, and $R^7$ is the same or different and independently hydrogen, or halogen, or $C_{1-6}$ alkyl. In more specific embodiments, each of $R^4$, $R^5$, $R^6$, and $R^7$ is hydrogen.

In particular embodiments, when the compound has substructure Ia, the compound is 2-(4-(4-bromophenylsulfonyl)-

2-phenyloxazol-5-ylthio)acetamide, 2-(4-(4-chlorophenyl-sulfonyl)-2-phenyloxazol-5-ylthio)acetamide, 2-(2-phenyl-4-tosyloxazol-5-ylthio)acetamide, 2-(2-phenyl-4-(phenylsulfonyl)oxazol-5-ylthio)acetamide, 2-(2-(4-fluorophenyl)-4-tosyloxazol-5-ylthio)acetamide, 2-(4-(4-chlorophenylsulfonyl)-2-(4-fluorophenyl)oxazol-5-ylthio) acetamide, 2-(2-(4-fluorophenyl)-4-(4-fluorophenylsulfonyl)oxazol-5-ylthio)acetamide, 2-(2-(4-fluorophenyl)-4-(phenylsulfonyl)oxazol-5-ylthio) acetamide, 2-(4-(4-bromophenylsulfonyl)-2-p-tolyloxazol-5-ylthio)acetamide, 2-(2-p-tolyl-4-tosyloxazol-5-ylthio) acetamide, 2-(4-(4-chlorophenylsulfonyl)-2-p-tolyloxazol-5-ylthio)acetamide, 2-(4-(phenylsulfonyl)-2-p-tolyloxazol-5-ylthio)acetamide, 2-(4-(4-chlorophenylsulfonyl)-2-(thiophen-2-yl)oxazol-5-ylthio)acetamide, 2-(2-(thiophen-2-yl)-4-tosyloxazol-5-ylthio)acetamide, 2-(4-(4-fluorophenylsulfonyl)-2-(thiophen-2-yl)oxazol-5-ylthio) acetamide, 2-(4-(phenylsulfonyl)-2-(thiophen-2-yl)oxazol-5-ylthio)acetamide, 2-(4-(4-chlorophenylsulfonyl)-2-(furan-2-yl)oxazol-5-ylthio)acetamide, 2-(4-(4-bromophenylsulfonyl)-2-(furan-2-yl)oxazol-5-ylthio) acetamide, or 2-(2-(furan-2-yl)-4-tosyloxazol-5-ylthio) acetamide.

In some embodiments of structure (I), when X is O, $R^1$ is N-benzylamino and each of $R^4$, $R^5$, $R^6$ and $R^7$ is hydrogen and the compound has a substructure of the following formula (Ib):

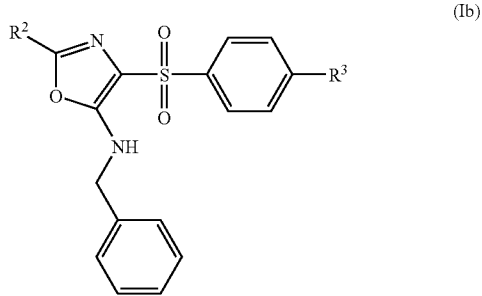

(Ib)

or pharmaceutically acceptable salts, prodrugs or stereoisomers thereof, wherein $R^3$ is hydrogen, halogen, or alkyl.

In certain embodiments, when the compound has substructure Ib, $R^3$ is hydrogen, halogen, or methyl. In more particular embodiments, $R^3$ is chloro. In other embodiments, when the compound has substructure Ib, $R^2$ is unsubstituted aryl; mono-substituted aryl wherein the substituent is meta or para to the linking carbon; or a substituted or unsubstituted heterocycle. In certain particular embodiments, $R^2$ is a substituted or unsubstituted five- or six-member heteroaryl having at least O or S; unsubstituted phenyl; or mono-substituted phenyl wherein the substituent is meta or para to the linking carbon and is halogen, $C_{1-6}$ alkyl, or $C_{1-6}$ alkoxyalkyl. In more specific embodiments, $R^2$ is phenyl substituted with fluoro.

In a specific embodiment, when the compound has substructure Ib, the compound is N-benzyl-4-(4-chlorophenyl-sulfonyl)-2-(2-fluorophenyl)oxazol-5-amine.

In further embodiments of structure (I), when X is O, $R^1$ is S—[N-(furan-2-yl-methyl)-2-mercaptoacetamidyl] and each of $R^4$, $R^5$, $R^6$ and $R^7$ is hydrogen and the compound has a substructure of the following formula (Ic):

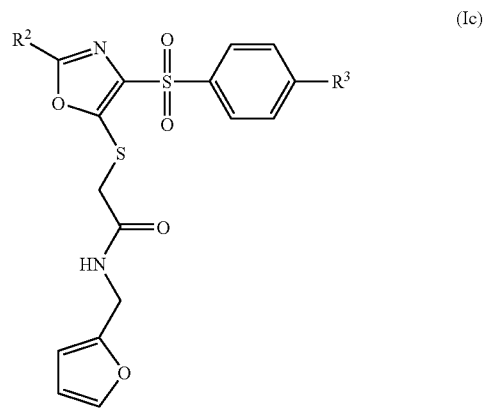

(Ic)

or pharmaceutically acceptable salts, prodrugs or stereoisomers thereof, wherein $R^3$ is hydrogen, halogen, or alkyl.

In certain embodiments, when the compound has substructure Ic, $R^3$ is hydrogen, halogen, or methyl. In more particular embodiments, $R^3$ is bromo or chloro. In other embodiments, when the compound has substructure Ic, $R^2$ is unsubstituted aryl; mono-substituted aryl wherein the substituent is meta or para to the linking carbon; or a substituted or unsubstituted heterocycle. In certain particular embodiments, $R^2$ is unsubstituted phenyl; or mono-substituted phenyl wherein the substituent is meta or para to the linking carbon and the substituent is halogen, $C_{1-6}$ alkyl, or $C_{1-6}$ alkoxy. In more specific embodiments, $R^2$ is unsubstituted phenyl.

In particular embodiments, when the compound has substructure Ic, the compound is 2-(4-(4-bromophenylsulfonyl)-2-phenyloxazol-5-ylthio)-N-(furan-2-ylmethyl)acetamide or 2-(4-(4-chlorophenylsulfonyl)-2-phenyloxazol-5-ylthio)-N-(furan-2-ylmethyl)acetamide.

In certain embodiments of structure (I), when X is O, $R^1$ is N-dimethylamino and each of $R^4$, $R^5$, $R^6$ and $R^7$ is hydrogen and the compound has a substructure of the following formula (Id):

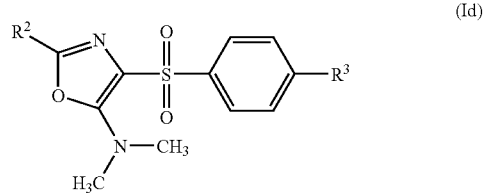

(Id)

or pharmaceutically acceptable salts, prodrugs or stereoisomers thereof, wherein $R^3$ is hydrogen, halogen, or alkyl.

In some embodiments, when the compound has substructure Id, $R^2$ is unsubstituted phenyl; or mono-substituted phenyl wherein the substituent is meta or para to the linking carbon and the substituent is halogen, $C_{1-6}$ alkyl, or $C_{1-6}$ alkoxy. In more particular embodiments, $R^2$ is phenyl substituted with chloro. In yet other more particular embodiments, $R^3$ is hydrogen.

In a particular embodiment, when the compound has substructure Id, the compound is 2-(2-chlorophenyl)-N,N-dimethyl-4-(phenylsulfonyl)oxazol-5-amine.

In further embodiments of structure (I), when X is O, $R^1$ is N-morpholino and each of $R^4$, $R^5$, $R^6$ and $R^7$ is hydrogen and the compound has a substructure of the following formula (Ie):

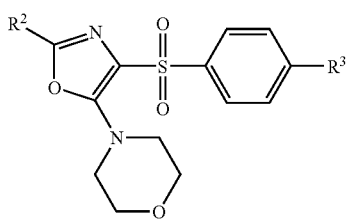

(Ie)

or pharmaceutically acceptable salts, prodrugs or stereoisomers thereof, wherein $R^3$ is hydrogen, halogen, or alkyl.

In certain embodiments, when the compound has substructure Ie, $R^2$ is unsubstituted phenyl; or mono-substituted phenyl wherein the substituent is meta or para to the linking carbon and the substituent is halogen, $C_{1-6}$ alkyl, or $C_{1-6}$ alkoxy. In more specific embodiments, $R^2$ is phenyl substituted with chloro or fluoro. In yet other more specific embodiments, $R^3$ is hydrogen or methyl.

In certain particular embodiments, when the compound has substructure Ie, the compound is 4-(2-(2-fluorophenyl)-4-(phenylsulfonyl)oxazol-5-yl)morpholine or 4-(2-(2-chlorophenyl)-4-tosyloxazol-5-yl)morpholine.

In some embodiments of structure (I), when X is O, $R^1$ is N-hexahydro-1-H-azepinyl and each of $R^4$, $R^5$, $R^6$ and $R^7$ is hydrogen and the compound has a substructure of the following formula (If):

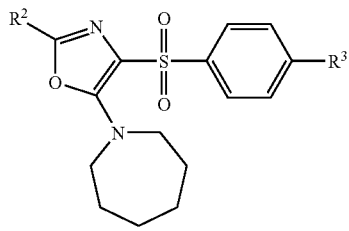

(If)

or a pharmaceutically acceptable salt, prodrug or stereoisomer thereof, wherein $R^3$ is hydrogen, halogen, or alkyl. In more particular embodiments, $R^3$ is hydrogen.

In certain embodiments, when the compound has substructure If, $R^2$ is unsubstituted phenyl; or mono-substituted phenyl wherein the substituent is meta or para to the linking carbon and the substituent is halogen, $C_{1-6}$ alkyl, or $C_{1-6}$ alkoxy. In further embodiments, when the compound has substructure If and the substituent is mono-substituted phenyl, the substituent is methyl, methoxy, or halogen. In more specific embodiments thereof, the halogen is fluoro.

In some particular embodiments, when the compound has substructure If, the compound is 5-(azepan-1-yl)-2-(2-methoxyphenyl)-4-(phenylsulfonyl)oxazole, 5-(azepan-1-yl)-4-(phenylsulfonyl)-2-p-tolyloxazole or 5-(azepan-1-yl)-2-(4-fluorophenyl)-4-(phenylsulfonyl)oxazole.

In certain embodiments of structure (I), when X is O, $R^1$ is S-mercaptomethyl and each of $R^4$, $R^5$, $R^6$ and $R^7$ is hydrogen and the compound has a substructure the following formula (Ig):

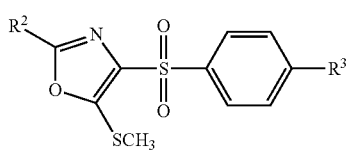

(Ig)

or pharmaceutically acceptable salts, prodrugs or stereoisomers thereof, wherein $R^3$ is hydrogen, halogen, or alkyl. In more specific embodiments, $R^3$ is chloro.

In some embodiments, when the compound has substructure Ig, $R^2$ is a five-membered heteroaryl having at least O or S; unsubstituted phenyl; or mono-substituted phenyl wherein the substituent is halogen or $C_{1-6}$ alkyl at a position meta or para to the linking carbon. In more particular embodiments, $R^2$ is furan-2-yl.

In a specific embodiment, when the compound has substructure Ig, the compound is 4-(4-chlorophenylsulfonyl)-2-(furan-2-yl)-5-(methylthio)oxazole.

In further embodiments of structure (I), $R^2$ is phenyl, 2-fluorophen-2-yl, 4-fluorophen-1-yl, 2-chlorophen-1-yl, 4-methylphen-1-yl, 2-methyoxyphen-1-yl, thiophene-2-yl, or furan-2-yl. In yet other embodiments of structure (I), $R^3$ is hydrogen, fluoro, chloro, bromo or methyl.

In certain embodiments of structure (I), X is NH. In more specific embodiments of structure (I), when X is NH, $R^1$ is S-mercaptomethyl and each of $R^4$, $R^5$, $R^6$ and $R^7$ is hydrogen and the compound has a substructure of the following formula (Ih):

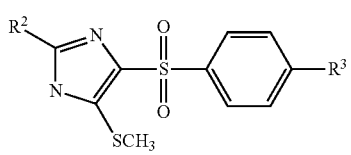

(Ih)

or pharmaceutically acceptable salts, prodrugs or stereoisomers thereof, wherein $R^2$ is unsubstituted phenyl; or mono-substituted phenyl wherein the substituent is meta or para to the linking carbon and the substituent is halogen, $C_{1-6}$ alkyl, or $C_{1-6}$ alkoxy; and wherein $R^3$ is hydrogen, halogen, or $C_{1-6}$ alkyl. In more specific embodiments, $R^2$ is mono-substituted phenyl wherein the substituent is methyl. In yet other more specific embodiments, $R^3$ is hydrogen or halogen.

In a specific embodiment, when the compound has substructure Ih, the compound is 5-(methylthio)-4-(phenylsulfonyl)-2-p-tolyl-1H-imidazole.

In further embodiments of structure (I), when X is NH, $R^1$ is sulfhydryl and each of $R^4$, $R^5$, $R^6$ and $R^7$ is hydrogen and the compound has a substructure of the following formula (Ii):

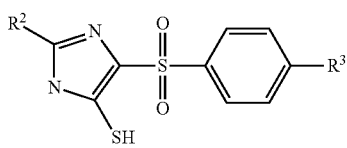

(Ii)

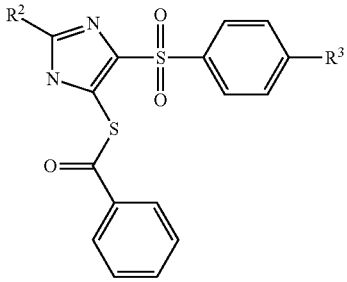

(Ij)

or pharmaceutically acceptable salts, prodrugs or stereoisomers thereof, wherein $R^2$ is unsubstituted phenyl, or monosubstituted phenyl wherein the substituent is meta or para to the linking carbon and the substituent is halogen, $C_{1-6}$ alkyl, or $C_{1-6}$ alkoxy; and wherein $R^3$ is hydrogen, halogen, or $C_{1-6}$ alkyl. In certain more particular embodiments, $R^2$ is unsubstituted phenyl. In yet other more particular embodiments, $R^3$ is hydrogen or methyl.

In a particular embodiment, when the compound has substructure Ii, the compound is 2-phenyl-4-tosyl-1H-imidazole-5-thiol.

In other embodiments of structure (I), when X is NH, $R^1$ is —S-benzothioate and each of $R^4$, $R^5$, $R^6$ and $R^7$ is hydrogen and the compound has a substructure of the following formula (Ij):

or pharmaceutically acceptable salts, prodrugs or stereoisomers thereof, wherein $R^2$ is unsubstituted phenyl; or monosubstituted phenyl wherein the substituent is meta or para to the linking carbon and the substituent is halogen, $C_{1-6}$ alkyl, or $C_{1-6}$ alkoxy; and wherein $R^3$ is hydrogen, halogen, or $C_{1-6}$ alkyl. In more specific embodiments, $R^2$ is unsubstituted phenyl. In other more specific embodiments, $R^3$ is hydrogen or halogen.

In a specific embodiment, when the compound has substructure Ij, the compound is S-2-phenyl-4-(phenylsulfonyl)-1H-imidazol-5-yl benzothioate.

In certain particular embodiments of structure (I), when X is NH, $R^1$ is S-mercaptomethyl; sulfhydryl; or —S-benzothioate. In further particular embodiments of structure (I), when X is NH, $R^2$ is phenyl or 4-methylphen-1-yl. In yet other particular embodiments of structure (I), when X is NH, $R^3$ is hydrogen or methyl.

In specific embodiments, the compounds of formula (I) and subgroups thereof described herein have the following structures.

| Compound # | Structure | Name |
|---|---|---|
| Urea$_{inh}$-101 | 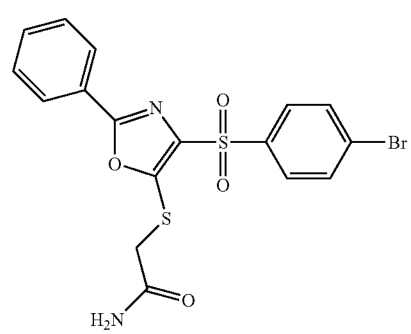 [SMILES: NC(=O)CSc1oc(-c2ccccc2)nc1S(=O)(=O)c1ccc(Br)cc1] | 2-(4-(4-bromophenylsulfonyl)-2-phenyloxazol-5-ylthio)acetamide |
| Urea$_{inh}$-102 | 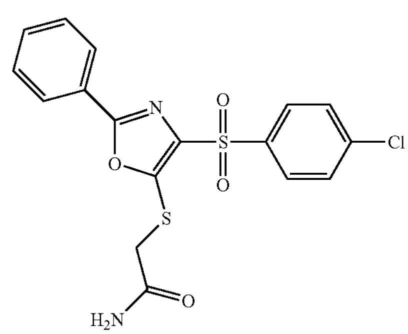 [SMILES: NC(=O)CSc1oc(-c2ccccc2)nc1S(=O)(=O)c1ccc(Cl)cc1] | 2-(4-(4-chlorophenylsulfonyl)-2-phenyloxazol-5-ylthio)acetamide |

-continued

| Compound # | Structure | Name |
|---|---|---|
| Urea$_{inh}$-103 | 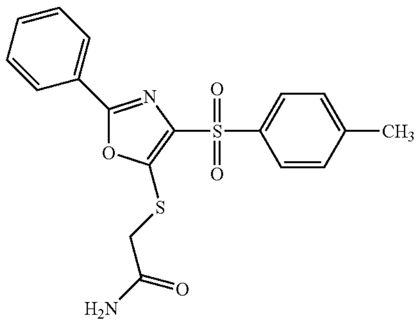 [SMILES: Cc1ccc(S(=O)(=O)c2nc(-c3ccccc3)oc2SCC(N)=O)cc1] | 2-(2-phenyl-4-tosyloxazol-5-ylthio)acetamide |
| Urea$_{inh}$-104 | 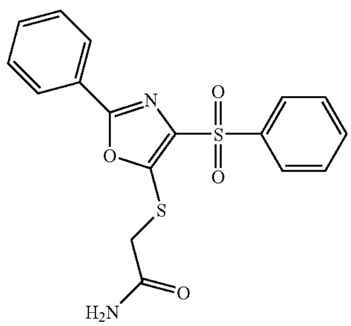 [SMILES: NC(=O)CSc1oc(-c2ccccc2)nc1S(=O)(=O)c1ccccc1] | 2-(2-phenyl-4-(phenylsulfonyf)oxazol-5-ylthio)acetamide |
| Urea$_{inh}$-105 | 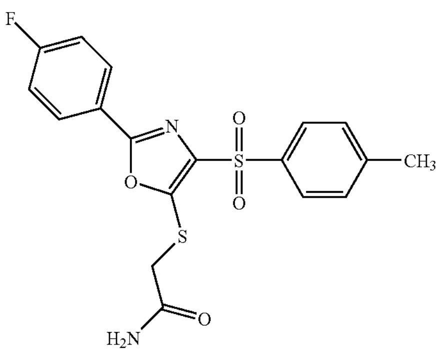 [SMILES: Cc1ccc(S(=O)(=O)c2nc(-c3ccc(F)cc3)oc2SCC(N)=O)cc1] | 2-(2-(4-fluorophenyl)-4-tosyloxazol-5-ylthio)acetamide |
| Urea$_{inh}$-106 | 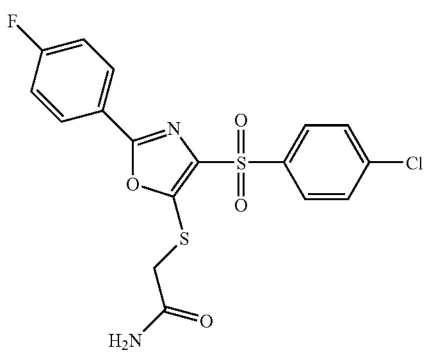 [SMILES: NC(=O)CSc1oc(-c2ccc(F)cc2)nc1S(=O)(=O)c1ccc(Cl)cc1] | 2-(4-(4-chlorophenylsulfonyl)-2-(4-fluorophenyl)oxazol-5-ylthio)acetamide |

-continued

| Compound # | Structure | Name |
|---|---|---|
| Urea$_{inh}$-107 | 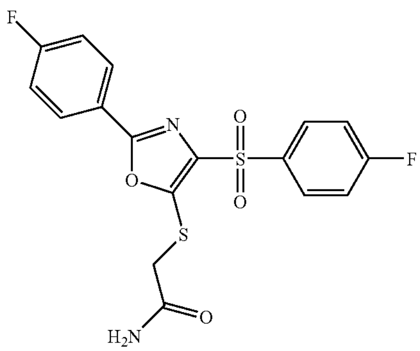 [SMILES: NC(=O)CSc1oc(-c2ccc(F)cc2)nc1S(=O)(=O)c1ccc(F)cc1] | 2-(2-(4-fluorophenyl)-4-(4-fluorophenylsulfonyl)oxazol-5-ylthio)acetamide |
| Urea$_{inh}$-108 | 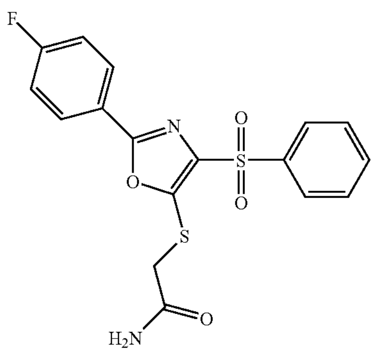 [SMILES: NC(=O)CSc1oc(-c2ccc(F)cc2)nc1S(=O)(=O)c1ccccc1] | 2-(2-(4-fluorophenyl)-4-(phenylsulfonyl)oxazol-5-ylthio)acetamide |
| Urea$_{inh}$-109 | 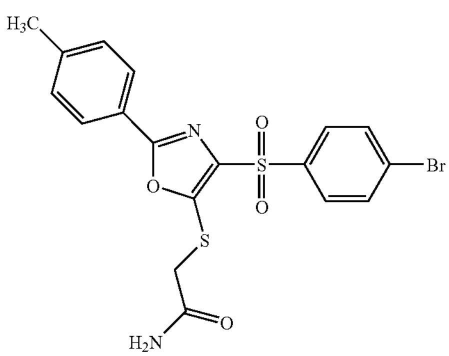 [SMILES: Cc1ccc(-c2nc(S(=O)(=O)c3ccc(Br)cc3)c(SCC(N)=O)o2)cc1] | 2-(4-(4-bromophenylsulfonyl)-2-p-tolyloxazol-5-ylthio)acetamide |
| Urea$_{inh}$-110 | 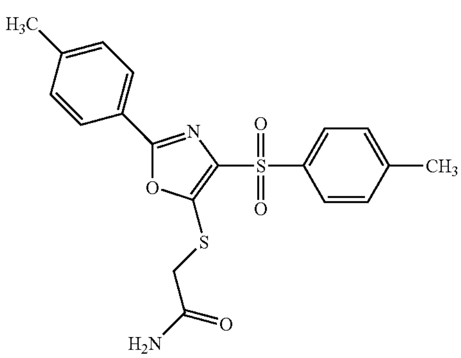 | 2-(2-p-tolyl-4-tosyloxazol-5-ylthio)acetamide |

-continued

| Compound # | Structure | Name |
|---|---|---|
| Urea_inh-111 | 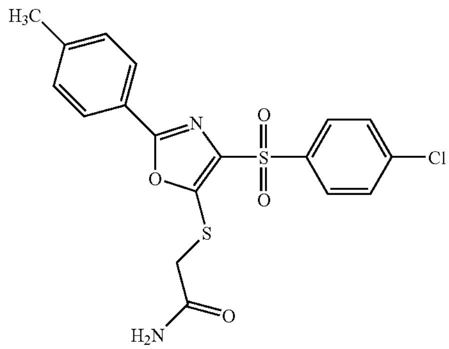 | 2-(4-(4-chlorophenylsulfonyl)-2-p-tolyloxazol-5-ylthio)acetamide |
| Urea_inh-112 | 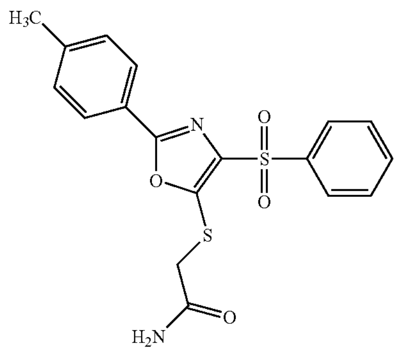 [SMILES: Cc1ccc(-c2nc(S(=O)(=O)c3ccccc3)c(SCC(N)=O)o2)cc1] | 2-(4-(phenylsulfonyl)-2-p-tolyloxazol-5-ylthio)acetamide |
| Urea_inh-113 | 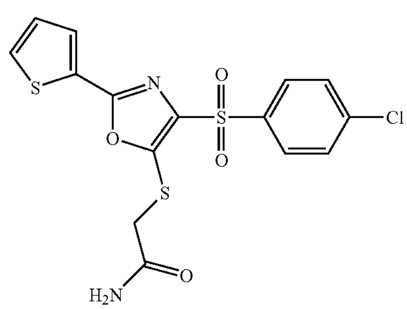 [SMILES: NC(=O)CSc1oc(-c2cccs2)nc1S(=O)(=O)c1ccc(Cl)cc1] | 2-(4-(4-chlorophenylsulfonyl)-2-(thiophen-2-yl)oxazol-5-ylthio)acetamide |
| Urea_inh-114 | 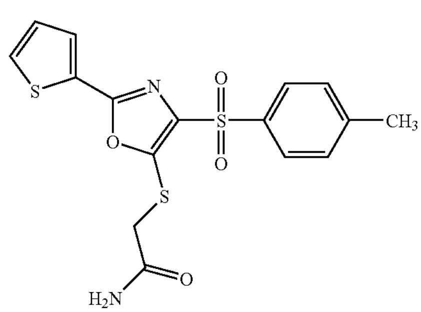 [SMILES: Cc1ccc(S(=O)(=O)c2nc(-c3cccs3)oc2SCC(N)=O)cc1] | 2-(2-(thiophen-2-yl)-4-tosyloxazol-5-ylthio)acetamide |

-continued

| Compound # | Structure | Name |
|---|---|---|
| Urea$_{inh}$-115 | | 2-(4-(4-fluorophenylsulfonyl)-2-(thiophen-2-yl)oxazol-5-ylthio)acetamide |
| Urea$_{inh}$-116 | | 2-(4-(phenylsulfonyl)-2-(thiophen-2-yl)oxazol-5-ylthio)acetamide |
| Urea$_{inh}$-117 | | 2-(4-(4-chlorophenylsulfonyl)-2-(furan-2-yl)oxazol-5-ylthio)acetamide |
| Urea$_{inh}$-118 | | 2-(4-(4-bromophenylsulfonyl)-2-(furan-2-yl)oxazol-5-ylthio)acetamide |
| Urea$_{inh}$-119 | | 2-(2-(furan-2-yl)-4-tosyloxazol-5-ylthio)acetamide |

-continued

| Compound # | Structure | Name |
|---|---|---|
| Urea$_{inh}$-120 | 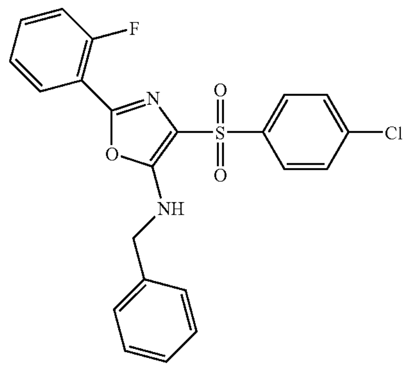 [SMILES: O=S(=O)(c1ccc(Cl)cc1)c1nc(-c2ccccc2F)oc1NCc1ccccc1] | N-benzyl-4-(4-chlorophenyl sulfonyl)-2-(2-fluorophenyl)oxazol-5-amine |
| Urea$_{inh}$-121 | 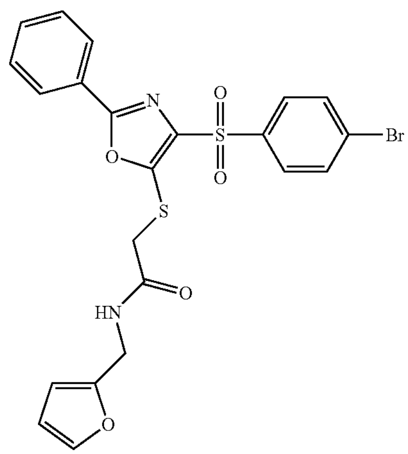 [SMILES: O=C(CSc1oc(-c2ccccc2)nc1S(=O)(=O)c1ccc(Br)cc1)NCc1ccco1] | 2-(4-(4-bromophenylsulfonyl)-2-phenyloxazol-5-ylthio)-N-(furan-2-ylmethyl)acetamide |
| Urea$_{inh}$-122 | 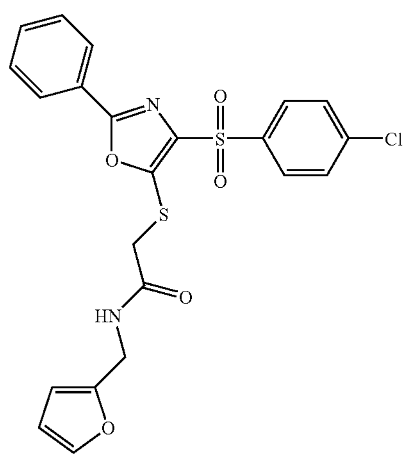 [SMILES: O=C(CSc1oc(-c2ccccc2)nc1S(=O)(=O)c1ccc(Cl)cc1)NCc1ccco1] | 2-(4-(4-chlorophenylsulfonyl)-2-phenyloxazol-5-ylthio)-N-(furan-2-ylmethyl)acetamide |
| Urea$_{inh}$-123 | 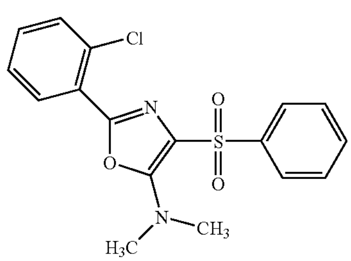 [SMILES: CN(C)c1oc(-c2ccccc2Cl)nc1S(=O)(=O)c1ccccc1] | 2-(2-chlorophenyl)-N,N-dimethyl-4-(phenylsulfonyl)oxazol-5-amine |

-continued

| Compound # | Structure | Name |
|---|---|---|
| Urea$_{inh}$-124 | 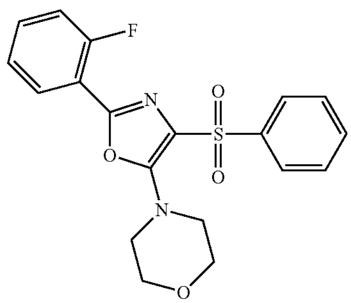 [SMILES: O=S(=O)(c1ccccc1)c1nc(-c2ccccc2F)oc1N1CCOCC1] | 4-(2-(2-fluorophenyl)-4-(phenylsulfonyl)oxazol-5-yl)morpholine |
| Urea$_{inh}$-125 | 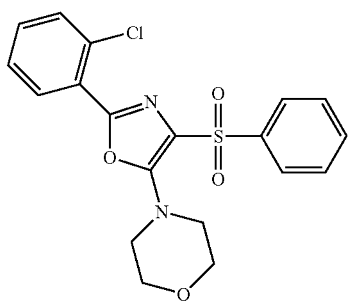 [SMILES: O=S(=O)(c1ccccc1)c1nc(-c2ccccc2Cl)oc1N1CCOCC1] | 4-(2-(2-chlorophenyl)-4-tosyloxazol-5-yl)morpholine |
| Urea$_{inh}$-126 | 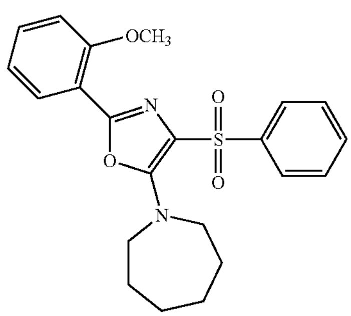 [SMILES: COc1ccccc1-c1nc(S(=O)(=O)c2ccccc2)c(N2CCCCCC2)o1] | 5-(azepan-1-yl)-2-(2-methoxyphenyl)-4-(phenylsulfonyl)oxazole |
| Urea$_{inh}$-127 | 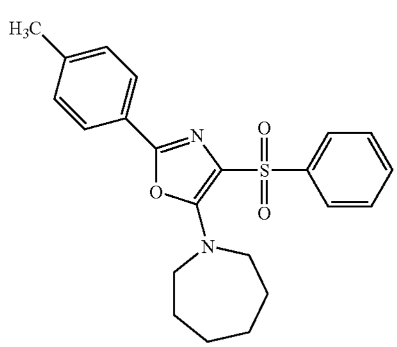 [SMILES: Cc1ccc(-c2nc(S(=O)(=O)c3ccccc3)c(N3CCCCCC3)o2)cc1] | 5-(azepan-1-yl)-4-(phenylsulfonyl)-2-p-tolyloxazole |

| Compound # | Structure | Name |
|---|---|---|
| Urea$_{inh}$-128 | 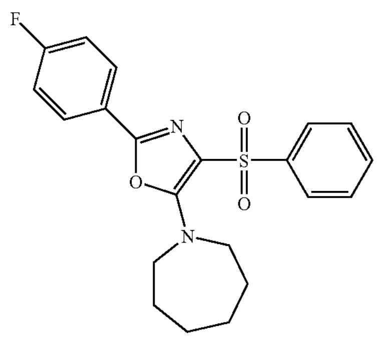 [SMILES: O=S(=O)(c1ccccc1)c1nc(-c2ccc(F)cc2)oc1N1CCCCCC1] | 5-(azepan-1-yl)-2-(4-fluorophenyl)-4-(phenylsulfonyl)oxazole |
| Urea$_{inh}$-129 | 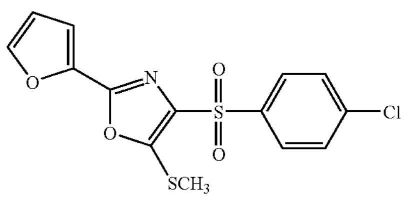 [SMILES: CSc1oc(-c2ccco2)nc1S(=O)(=O)c1ccc(Cl)cc1] | 4-(4-chlorophenylsulfonyl)-2-(furan-2-yl)-5-(methylthio)oxazole |
| Urea$_{inh}$-130 | 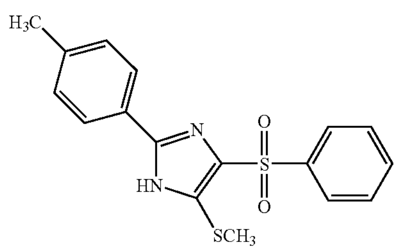 [SMILES: CSc1[nH]c(-c2ccc(C)cc2)nc1S(=O)(=O)c1ccccc1] | 5-(methylthio)-4-(phenylsulfonyl)-2-p-tolyl-1H-imidazole |
| Urea$_{inh}$-131 | 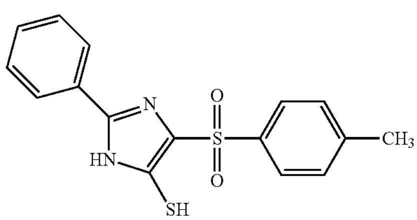 [SMILES: Cc1ccc(S(=O)(=O)c2nc(-c3ccccc3)[nH]c2S)cc1] | 2-phenyl-4-tosyl-1H-imidazole-5-thiol |
| Urea$_{inh}$-132 | 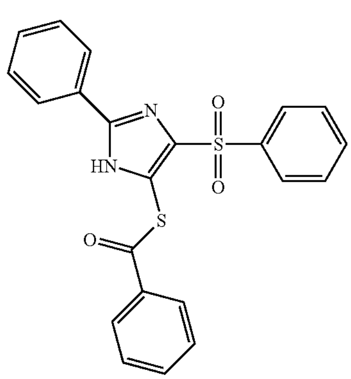 [SMILES: O=C(Sc1[nH]c(-c2ccccc2)nc1S(=O)(=O)c1ccccc1)c1ccccc1] | S-2-phenyl-4-(phenylsulfonyl)-1H-imidazol-5-yl benzothioate |

Definitions

Certain chemical groups named herein are preceded by a shorthand notation indicating the total number of carbon atoms that are to be found in the indicated chemical group. For example; $C_1$-$C_6$ alkyl describes an alkyl group, as defined below, having a total of 1 to 6 carbon atoms, and $C_3$-$C_{12}$ cycloalkyl describes a cycloalkyl group, as defined below, having a total of 3 to 12 carbon atoms. The total number of carbons in the shorthand notation does not include carbons that may exist in substituents of the group described. In addition to the foregoing, as used herein, unless specified to the contrary, the following terms have the meaning indicated.

"Alkyl" means a straight chain or branched, noncyclic or cyclic, unsaturated or saturated aliphatic hydrocarbon containing from 1 to 12 carbon atoms, while the terms "lower alkyl" and "$C_{1-6}$ alkyl" have the same meaning as alkyl but contain from 1 to 6 carbon atoms. Representative saturated straight chain alkyls include methyl, ethyl, n-propyl, n-butyl, n-pentyl, n-hexyl, and the like, while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, —CH$_2$cyclopropyl, —CH$_2$cyclobutyl, —CH$_2$cyclopentyl, —CH$_2$cyclohexyl, and the like; unsaturated cyclic alkyls include cyclopentenyl and cyclohexenyl, and the like. Cyclic alkyls, also referred to as "homocyclic rings," include di- and poly-homocyclic rings such as decalin and adamantyl. Unsaturated alkyls contain at least one double or triple bond between adjacent carbon atoms (referred to as an "alkenyl" or "alkynyl," respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; representative straight chain and branched alkynyls include acetylenyl, propynyl, 1-butynyl, 2-butynyl, 1-pentynyl, 2-pentynyl, 3-methyl-1 butynyl, and the like. It is understood that within the context of the current invention, the term "alkyl" is taken to comprise unsubstituted alkyl and substituted alkyl as defined herein, unless otherwise specified.

As used herein, the term "substituted" in the context of alkyl, aryl, arylalkyl, heterocycle, and heterocycloalkyl means that at least one hydrogen atom of the alky, aryl, arylalkyl, heterocycle or heterocycloalkyl moiety is replaced with a substituent. In the instance of an oxo substituent ("=O") two hydrogen atoms are replaced. A "substituent" as used within the context of this invention includes oxo, halogen, hydroxy, cyano, nitro, amino, alkylamino, dialkylamino, alkyl, alkoxy, thioalkyl, haloalkyl, substituted alkyl, heteroalkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocycloalkyl, substituted heterocycloalkyl, —NR$_a$R$_b$, —NR$_a$C(=O)R$_b$, —NR$_a$C(=O)NR$_a$R$_b$, —NR$_a$C(=O)OR$_b$—NR$_a$S(=O)$_2$R$_b$, —OR$_a$, —C(=O)R$_a$—C(=O)OR$_a$, —C(=O)NR$_a$R$_b$, —OCH$_2$C(=O)NR$_a$R$_b$, —OC(=O)NR$_a$R$_b$, —SH, —SR$_a$, —SOR$_a$, —S(=O)$_2$NR$_a$R$_b$, —S(=O)$_2$R$_a$, —SR$_a$C(=O)NR$_a$R$_b$, —OS(=O)$_2$R$_a$ and —S(=O)$_2$OR$_a$, wherein R$_a$ and R$_b$ are the same or different and independently hydrogen, alkyl, haloalkyl, substituted alkyl, alkoxy, aryl, substituted aryl, arylalkyl, substituted arylalkyl, arylalkoxy, heteroaryl, substituted heteroaryl, heteroarylalkyl, substituted heteroarylalkyl, heterocycle, substituted heterocycle, heterocycloalkyl or substituted heterocycloalkyl.

Representative substituents include (but are not limited to) alkoxy (i.e., alkyl-O—, e.g., methoxy, ethoxy, propoxy, butoxy, pentoxy), aryloxy (e.g., phenoxy, chlorophenoxy, tolyloxy, methoxyphenoxy, benzyloxy, alkyloxycarbonylphenoxy, alkyloxycarbonyloxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkyloxycarbonyl-phenylthio), aminyl (e.g., amino, mono- and di-$C_1$-$C_3$ alkanylamino, methylphenylamino, methylbenzylamino), $C_1$-$C_3$ alkanylamido, acylamino, carbamamido, ureido, guanidino, nitro and cyano. Moreover, any substituent may have from 1-5 further substituents attached thereto.

"Aryl" means an aromatic carbocyclic moiety such as phenyl or naphthyl (1- or 2-naphthyl).

"Arylalkyl" means an alkyl having at least one alkyl hydrogen atom replaced with an aryl moiety, such as —CH$_2$-phenyl, —CH=CH-phenyl, —C(CH$_3$)=CH-phenyl, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —CH$_2$pyridinyl, —CH$_2$pyrimidinyl, and the like.

"Heterocycle" (also referred to herein as a "heterocyclic ring") means a 4- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined herein. Thus, in addition to the heteroaryls listed above, heterocycles also include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "optionally substituted" as used in the context of an optionally substituted heterocycle (as well heteroaryl) means that at least one hydrogen atom is replaced with a substituent. In the case of a keto substituent ("—C(=O)—") two hydrogen atoms are replaced. When substituted, one or more of the above groups are substituted. "Substituents" within the context of this invention are also described above and include halogen, hydroxy, cyano, nitro, amino, alkylamino, dialkylamino, alkyl, alkoxy, alkylthio, haloalkyl, aryl, arylalkyl, heteroaryl, heteroarylalkyl, heterocycle and heterocycloalkyl, as well as —NR$_a$R$_b$, —NR$_a$C(=O)R$_b$, —NR$_a$C(=O)NR$_a$R$_b$, —NR$_a$C(=O)OR$_b$—NR$_a$S(=O)$_2$R$_b$, —OR$_a$, —C(=O)R$_a$—C(=O)OR$_a$, —C(=O)NR$_a$R$_b$, —OCH$_2$C(=O)NR$_a$R$_b$, —OC(=O)NR$_a$R$_b$, —SH, —SR$_a$, —SOR$_a$, —S(=O)$_2$NR$_a$R$_b$, —S(=O)$_2$R$_a$, —OS(=O)$_2$R$_a$ and —S(=O)$_2$OR$_a$. In addition, the above substituents may be further substituted with one or more of the above substituents, such that the substituent is a substituted alkyl, substituted aryl, substituted arylalkyl, substituted heterocycle or substituted heterocycloalkyl. $R_a$ and $R_b$ in this context may be the same or different and independently hydrogen, alkyl, haloalkyl, substituted alkyl, alkoxy, aryl, substituted aryl, arylalkyl, substituted arylalkyl, heterocycle (including heteroaryl), substituted heterocycle (including substituted heteroaryl), heterocycloalkyl, or substituted heterocycloalkyl.

"Heterocycloalkyl" means an alkyl having at least one alkyl hydrogen atom replaced with a heterocycle, such as —CH$_2$morpholinyl, —CH$_2$CH$_2$piperidinyl, —CH$_2$azepinyl, —CH$_2$pirazineyl, —CH$_2$pyranyl, —CH$_2$furanyl, —CH$_2$pyrrolidinyl, and the like.

"Homocycle" (also referred to herein as "homocyclic ring") means a saturated or unsaturated (but not aromatic) carbocyclic ring containing from 3-7 carbon atoms, such as cyclopropane, cyclobutane, cyclopentane, cyclohexane, cycloheptane, cyclohexene, and the like.

"Halogen" or "halo" means fluoro, chloro, bromo, and iodo.

"Haloalkyl," which is an example of a substituted alkyl, means an alkyl having at least one hydrogen atom replaced with halogen, such as trifluoromethyl and the like.

"Haloaryl," which is an example of a substituted aryl, means an aryl having at least one hydrogen atom replaced with halogen, such as 4-fluorophenyl and the like.

"Alkoxy" means an alkyl moiety attached through an oxygen bridge (i.e., —O-alkyl) such as methoxy, ethoxy, and the like.

"Haloalkoxy," which is an example, of a substituted alkoxy, means an alkoxy moiety having at least one hydrogen atom replaced with halogen, such as chloromethoxy and the like.

"Alkoxydiyl" means an alkyl moiety attached through two separate oxygen bridges (i.e., —O-alkyl-O—) such as —O—CH$_2$—O—, —O—CH$_2$CH$_2$—O—, —O—CH$_2$CH$_2$CH$_2$—O—, —O—CH(CH$_3$)CH$_2$CH$_2$—O—, —O—CH$_2$C(CH$_3$)$_2$CH$_2$—O—, and the like.

"Alkanediyl" means a divalent alkyl from which two hydrogen atoms are taken from the same carbon atom or from different carbon atoms, such as —CH$_2$—, —CH$_2$CH$_2$—, —CH$_2$CH$_2$CH$_2$—, —CH(CH$_3$)CH$_2$CH$_2$—, —CH$_2$C(CH$_3$)$_2$CH$_2$—, and the like.

"Thioalkyl" means an alkyl moiety attached through a sulfur bridge (i.e., —S-alkyl) such as methylthio, ethylthio, and the like.

"Alkylamino" and "dialkylamino" mean one or two alkyl moieties attached through a nitrogen bridge (i.e., —N-alkyl) such as methylamino, ethylamino, dimethylamino, diethylamino, and the like.

"Arylalkylamino" means an alkylamino having at least one alkyl hydrogen atom replaced with an aryl moiety, such as —NHCH$_2$-phenyl, and the like.

"Arylsulfonyl" is SO$_2$ bonded directly to an aryl group such as —SO$_2$-phenyl, and the like.

"Carbamate" is $R_aOC(=O)NR_aR_b$.

"Cyclic carbamate" means any carbamate moiety that is part of a ring.

"Carbamoyloxy" refers to the —OC(=O)NR$_a$R$_b$ radical.

"Carbamamido" refers to the —NR$_a$C(=O)NR$_a$R$_b$.

"Ureido" refers to the —NHC(=O)NH$_2$ radical.

"Amidyl" or "amido" refers to the —C(=O)NR$_a$R$_b$ radical.

"Hydroxyl" refers to the —OH radical.

"Sulfhydryl", "mercapto" or "thio" refers to the —SH radical.

"Acylthio" refers to the —C(=O)SH radical.

"Amino" refers to the —NH$_2$ radical.

"Aminyl" refers to the —NR$_a$R$_b$ radical.

"Acylamino" refers to the —NC(=O)R$_a$R$_b$ radical.

"Guanidino" refers to the —NR$_a$(C=NRa)NR$_a$R$_b$ radical.

"Nitro" refers to the —NO$_2$ radical.

"Imino" refers to the =NH substituent.

"Thioxo" refers to the =S substituent.

"Cyano" refers to the —CN radical.

"Carboxy" refers to the —C(=O)OH radical.

The compounds described herein may generally be used as the free acid or free base. Alternatively, the compounds may be used in the form of acid or base addition salts. Acid addition salts of the free base amino compounds may be prepared according to methods well known in the art, and may be formed from organic and inorganic acids. Suitable organic acids include (but are not limited to) maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include (but are not limited to) hydrochloric, hydrobromic, sulfuric, phosphoric, and nitric acids. Base addition salts of the free acid compounds of the compounds described herein may also be prepared by methods well known in the art, and may be formed from organic and inorganic bases. Suitable inorganic bases included (but are not limited to) the hydroxide or other salt of sodium, potassium, lithium, ammonium, calcium, magnesium, iron, zinc, copper, manganese, aluminum, and the like, and organic bases such as substituted ammonium salts. Thus, the term "pharmaceutically acceptable salt" of structure (I), as well as any and all substructures described herein is intended to encompass any and all pharmaceutically suitable salt foams.

Also contemplated are prodrugs of any of the compounds described herein. Prodrugs are any covalently bonded carriers that release a compound of structure (I), as well as any of the substructures herein, in vivo when such prodrug is administered to a subject. Prodrugs are generally prepared by modifying functional groups in a way such that the modification is cleaved, either by routine manipulation or by an in vivo process, yielding the parent compound. Prodrugs include, for example, compounds described herein when, for example, hydroxy or amine groups are bonded to any group that, when administered to a subject, is cleaved to form the hydroxy or amine groups. Thus, representative examples of prodrugs include (but are not limited to) acetate, formate and benzoate derivatives of alcohol and amine functional groups of the compounds of structure (I), as well as any of the substructures herein. Further, in the case of a carboxylic acid (—COOH), esters may be employed, such as methyl esters, ethyl esters, and the like. Prodrug chemistry is conventional to and routinely practiced by a person having ordinary skill in the art.

Prodrugs are typically rapidly transformed in vivo to yield the parent compound of the invention, for example, by hydrolysis in blood. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam)). A discussion of prodrugs is provided in Higuchi, T., et al., "Pro-drugs as Novel Delivery Systems," A.C.S. Symposium Series, Vol. 14, and in Bioreversible Carriers in Drug Design, Ed. Edward B. Roche, American Pharmaceutical Association and Pergamon Press, 1987, both of which are incorporated in full by reference herein.

With regard to stereoisomers, the compounds of structure (I), as well as any substructure herein, may have one or more chiral centers and may occur in any isomeric form, including racemates, racemic mixtures, and as individual enantiomers or diastereomers. In addition, the compounds of structure (I), as well as any substructure thereof, include E and Z isomers of all double bonds. All such isomeric forms of the compounds are included and contemplated, as well as mixtures thereof. Furthermore, some of the crystalline forms of any compound described herein may exist as polymorphs, which are also included and contemplated by the present disclosure. In addition, some of the compounds may form solvates with water or other organic solvents. Such solvates are similarly included within the scope of compounds and compositions described herein.

In general, the compounds used in the reactions described herein may be made according to organic synthesis techniques known to those skilled in this art, starting from commercially available chemicals and/or from compounds described in the chemical literature. "Commercially available chemicals" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hanover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

Methods known to one of ordinary skill in the art may be identified through various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds of the present invention, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000) Wiley-Interscience, ISBN: 0-471-31824-8; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the present invention is P. H. Stahl & C. G. Wermuth "Handbook of Pharmaceutical Salts", Verlag Helvetica Chimica Acta, Zurich, 2002.

Synthesis of Phenylsulfoxyoxazole, Phenylsulfoxyimidazole, and Phenylsulfoxythiazole Compounds The following is an exemplary reaction scheme for synthesizing the compounds disclosed herein.

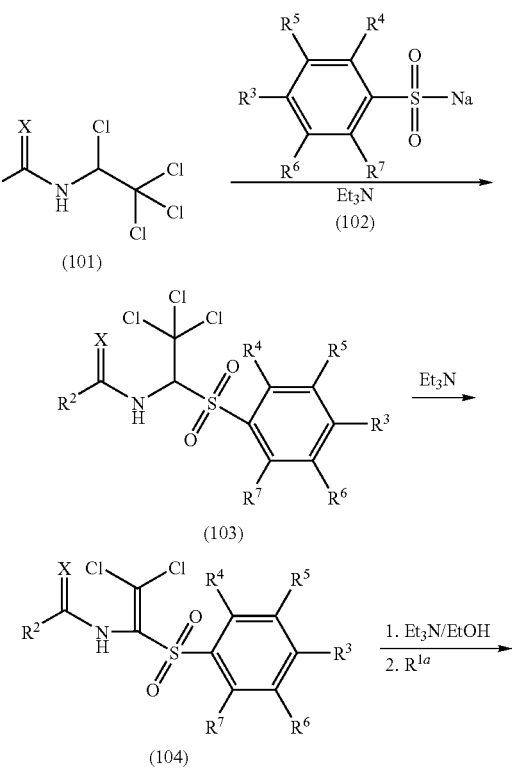

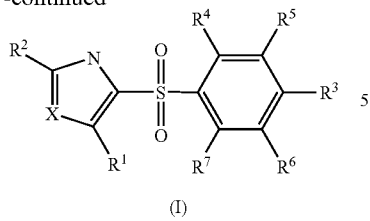

(I)

Appropriately substituted compounds of formula (101) and formula (102) are commercially available or can be prepared according to methods and techniques with which a person skilled in the art is familiar. A compound of formula (101) may be combined with a compound of formula (102) in the presence of a base, such as triethylamine ($Et_3N$), to form a compound of formula (103). Further, in the presence of a base, such as triethylamine, a compound of formula (103) forms a compound of formula (104). A compound of formula (104) combined with an appropriate base, such as triethylamine, in the presence of a solvent, such as ethanol (EtOH), followed by treatment with $R^{1a}$, wherein $R^{1a}$ is an appropriate $R^1$ containing reagent, yields compounds of formula (I). The substituents, X, $R^1$, $R^2$, $R^3$, $R^4$, $R^5$, $R^6$, and $R^7$ are the same as described above. One skilled in the art will appreciate that the $R^{1a}$ reagent encompasses any reagent such that base treatment of compounds of formula 104 followed by reaction with $R^{1a}$ yields compounds of formula (I). Examples of $R^{1a}$ reagents include, but are not limited to, sulfhydryl, heterocyclic, and aminyl groups. One skilled in the art will also appreciate that in some embodiments further reaction of the compound of formula (I) may be required to obtain the desired structure.

Reaction scheme 2 depicts an exemplary reaction scheme for synthesizing compounds of structure (Ik) disclosed herein.

Reaction Scheme 2

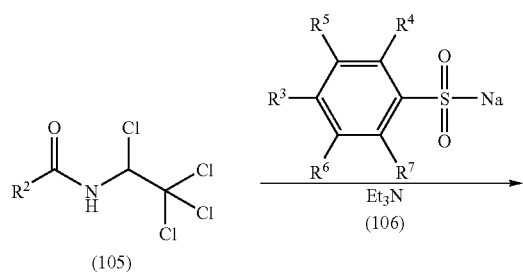

(105)

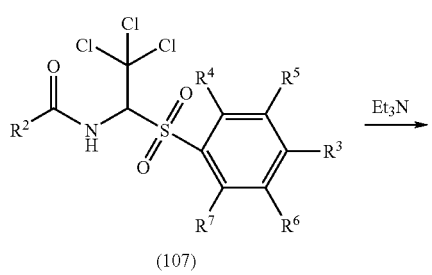

(107)

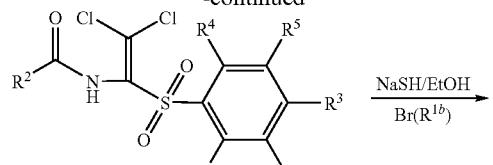

(108)

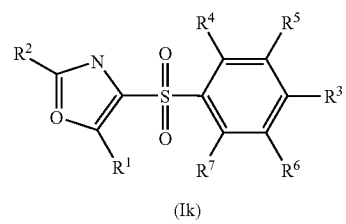

(Ik)

Appropriately substituted compounds of formula (105) and formula (106) are commercially available or can be prepared according to methods and techniques with which a person skilled in the art is familiar. A compound of formula (105) may be combined with a compound of formula (106) in the presence of triethylamine ($Et_3N$) to form a compound of formula (107). Further, in the presence of triethylamine a compound of formula (107) forms a compound of formula (108). A compound of formula (108) combined with NaSH and ethanol (EtOH) followed by treatment with Br($R^{1b}$) yields compounds of formula (Ik). One skilled in the art will recognize that where $R^1$ is hydrogen treatment with Br($R^{1b}$) is not required. The substituents, X, $R^1$, $R^2$, $R^3$, $R^4$, $R^5$, $R^6$, and $R^7$ are the same as described above. $R^{1b}$ may be any one of the following: $C_{1-6}$ alkyl, substituted or unsubstituted carboxyphenyl(i.e., —C(=O)-phenyl), —$(CH_2)_nC$(=O)$NHR^{10}$ wherein n is 1 to 6 and $R^{10}$ is hydrogen, straight-chain $C_{1-6}$ alkyl, arylalkyl, or heterocyclealkyl.

Inhibition of Urea Transport

Provided herein are methods for using the phenylsulfoxyoxazole, phenylsulfoxyimidazole, and phenylsulfoxythiazole compounds having the structure (I) and substructures (Ia)-(Ij). As described in detail herein, methods are provided for treating a disease, disorder, or condition associated with aberrant transport of a neutrally charged solute in a subject by administering to the subject in need thereof a pharmaceutical composition comprising at least one of the compounds having the structure (I) and substructures (Ia)-(Ij) described above. In a particular embodiment, the compounds and compositions described herein may treat a disease, disorder, or condition associated with aberrant transport of urea by a urea transporter. The compound may specifically inhibit all urea transporters or may interact with and inhibit only one subfamily of urea transporter (i.e., either UT-A transporters or UT-B transporters). The compounds described herein may specifically inhibit at least one of the UT-A isoforms (e.g., UT-A1, UT-A2, UT-A3, UT-A4, UT-A5).

The compounds having the structure (I) and substructures (Ia)-(Ij) described herein may be used to alter (i.e., increase or decrease in a statistically significant or biologically significant manner) transport of urea across a cell membrane by at least one urea transporter. In particular embodiments, transport activity of at least one urea transporter is inhibited, thus the compounds are capable of preventing, blocking, or decreasing transport of urea across a cell membrane. Methods are provided for an in vitro assay in which a cell comprising at least one urea transporter is contacted (combined, mixed, or in some manner permitted to interact) with a composition comprising at least one compound having the structure (I) or any one of the substructures described herein. In one embodiment, at least one compound described herein inhibits transport of urea by a UT-B transporter. In another embodiment, at least one compound having structure (I) or any substructure described herein inhibits the capability of a UT-A transporter to transport urea. In particular embodiments, the UT-A transporter is at least one of UT-A1, UT-A2, UT-A3, UT-A4, and UT-A5. In certain embodiments, the cell is a renal cell, a brain cell, a red blood cell, or a testis cell. In a particular embodiment, the cell is a renal cell. In another particular embodiment, the cell is a red blood cell, which comprises at least a UT-B transporter.

Urea transporters (UTs) are transmembrane proteins that transport urea across cellular membranes. UTs may be expressed in such tissues as the outer and inner medulla of the kidney, erythropoietic tissue, testis and hepatocytes. One function of UTs is production of concentrated urea, which is critical for retention of water.

Urea is generated as the major end product of hepatic nitrogen metabolism and is excreted primarily by the kidney. Urea and sodium chloride are the major solutes in the hyperosmolar renal medulla. In the antidiuretic kidney, urea is greatly concentrated with respect to plasma (up to 100 times in humans and 250 times in rodents) by countercurrent multiplication and exchange mechanisms (Bankir et al., *In The Kidney* (6th Edition), pages 637-679, Brenner, B M, ed., (WB Saunders Company, Philadelphia, Pa.) (2000)). Of central importance to these mechanisms is intrarenal urea recycling, which requires facilitated urea transport by molecular urea transporters (UTs). UTs are comprised of two major subfamilies encoded by different genes (UT-A and UT-B) (see, e.g., Bagnasco, *Am. J. Physiol.* 284:F3-F10 (2003); Shayakul et al., *Pflügers Arch.* 447:603-609 (2004)). In kidney, a single UT-B isoform is expressed in vasa recta while several splice variant UT-A-type transporters are expressed in kidney tubule epithelia (see, e.g., Sands, *Curr. Opin. Nephrol. Hypertens.* 13:525-32 (2004)). See also Karakashian et al., *J. Am. Soc. Nephrol.* 10: 230 37 (1999); Sands, *Mt Sinai J. Med.* 67:112 19 (2000); and Leroy et al., *Biochem. Biophys. Res. Commun.* 271:368-73 (2000).

Five UT-A urea transporter isoforms (UT-A1, UT-A2, UT-A3, UT-A4, and UT-A5) are encoded by alternatively splicing of the Slc14A2 gene (see, e.g., Bagnasco et al., *Am. J. Physiol. Renal Physiol.* 281:F400-F406 (2001); Shayakul et al., *Pflugers Arch.* 447:603-609 (2004); Bagnasco, *Pflugers Arch.* 450:217-26 (2005); Sands, *Curr. Opin. Nephrol. Hypertens.* 13:525-32 (2004); Bagnasco, *Am. J. Physiol. Renal Physiol.* 284:F3-F10 (2003); Sands et al. *Am. J. Physiol.* 273:F321-39 (1997); Sands, *Annu. Rev. Physiol.* 65:543-66 (2003)). The Slc14A1 gene encodes a single UT-B isoform (see, e.g., Sands, *Curr. Opin. Nephrol. Hypertens.* 13:525-32 (2004); Lucien et al., *J. Biol. Chem.* 273:12973-80 (1998); Bagnasco, *Am. J. Physiol. Renal Physiol.* 284:F3-F10 (2003); Sidoux et al., *J. Biol. Chem.* 274:30228-35 (1999); see also e.g., Tsukaguchi et al., *J Clin Invest.* 99:1506-15 (1997)).

In one embodiment, methods are provided for altering (i.e., increasing or decreasing in a statistically significant or biologically significant manner) transport of urea across a cell membrane by a urea transporter in a cell. Such methods comprise contacting (i.e., combining, mixing or in some manner permitting interaction with) the cell and any one or more (i.e., at least one) of the compounds having the structure (I) and substructures (Ia)-(Ij) described herein or a composition comprising at least one or more of such compounds. The compounds described herein are capable of inhibiting transport of urea by at least one urea transporter (e.g., a UT-B) in a cell in vivo (i.e., in an animal, including a human) or in vitro in an assay method, for example.

In a specific embodiment, a method is provided for inhibiting transport of urea across a cell membrane, which method comprises contacting (i.e., combining, mixing or in some manner permitting interaction with) a cell with at least one compounds having the structure (I) and substructures (Ia)-(Ij) or composition comprising a compound as described herein, wherein the cell comprises at least one urea transporter. The compounds described herein inhibit (i.e., reduce, abrogate, prevent, or decrease in a statistically significant or biologically significant manner) the capability of at least one urea transporter to transport urea across a cell membrane. A compound described herein may specifically interact with all urea transporters or may interact with only one subfamily of urea transporter (i.e., either UT-A transporters or UT-B transporters). Alternatively, the compound may specifically interact with at least one but not all of UT-A transporters. In a particular embodiment, the compounds inhibit a UT-B transporter.

Compounds having the structure (I) and substructures (Ia)-(Ij) inhibit the capability of at least one urea transporter to transport urea across a cell membrane. The transporter may be endogenously expressed by the cell (i.e., the genome of the cell comprises a nucleotide sequence that encodes the transporter, which is transcribed into mRNA that is translated), or the transporter may be recombinantly expressed in the cell (i.e., the cell comprises an exogenous polynucleotide that directs the expression of the transporter polypeptide). In a particular embodiment, the transporter is located in the outer cell membrane and is capable of transporting a solute into the cell from the extracellular environment or space (influx) and out of the cell into the extracellular environment or space (efflux).

In a particular embodiment, the compound inhibits (i.e., blocks, prevents, reduces, or decreases in a statistically or biologically significant manner) the capability of at least one urea transporter to transport urea across a cell membrane and thus inhibits urea influx and/or efflux. The compound may inhibit the transport activity of the transporter by binding to the transporter such that the compound inhibits transport of urea into the cell from the extracellular space, and/or the compound may bind to the transporter such that transport of urea out of the cell into the extracellular space is inhibited.

Cells may be obtained or derived from a biological sample. A biological sample as used herein refers in certain embodiments to a sample containing at least one cell or a plurality of cells that endogenously or exogenously expresses at least one urea transporter. A biological sample may be a blood sample, such as whole blood or a cellular fraction of whole blood, biopsy specimen, body fluids that contain cells that express at least one transporter (e.g., lung lavage, ascites, mucosal washings, synovial fluid), bone marrow, lymph nodes, tissue explant, organ culture, or any other tissue or cell preparation from a subject or a biological source. A sample may further refer to a tissue or cell preparation in which the morphological integrity or physical state of the tissue has been disrupted, for example, by dissection, dissociation, solubilization, fractionation, homogenization, biochemical or chemical extraction. The subject or biological source may be a human or non-human animal, a primary cell culture (e.g., kidney cells or other cells that endogenously express a transporter), or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiable cell lines, transformed cell lines, and the like.

The cells comprising a urea transporter that is inhibited by the compounds and compositions described herein include cells that endogenously express a urea transporter polypeptide. Exemplary cells that endogenously express a urea transporter include but are not limited to a renal cell, a brain cell, a red blood cell, a liver cell, or a testis cell. Transport of urea by urea transporters and transport of water by aquaporins are opposing processes in such cells. An exemplary cell that may be used in the methods described herein and that expresses a urea transporter is a red blood cell (i.e., erythrocyte), which endogenously expresses the urea transporter UT-B (also referred to as the Kidd blood group antigen). Red blood cells also express an aquaporin, AQP1.

Alternatively, the cells (which may be any one of a renal cell, a brain cell, a red blood cell, a liver cell, or a testis cell or other cell) may comprise an exogenous polynucleotide that encodes a urea transporter polypeptide. The cell may be transfected, transformed, or transduced with a recombinant expression vector, which comprises a polynucleotide that is capable of directing expression of at least one urea transporter. To direct expression of at least one transporter, the polynucleotide comprises a nucleotide sequence that encodes at least one urea transporter, which nucleotide sequence is operatively linked to at least one expression control sequence (e.g., a promoter, enhancer, transcriptional control element, and the like). Recombinant expression vectors may be prepared according to methods and techniques with which a person skilled in the molecular biology art is familiar. An exemplary cell line that may be transfected with a recombinant expression vector comprising a polynucleotide that directs expression of a urea transporter or other transport includes Madin-Darby canine kidney cells (MDCK).

Cells may be obtained or derived from any one of a number of animals, including mammals. Mammalian cells may be obtained or may have originated from humans; non-human primates; rodents such as mice, rats, or rabbits; cats (feline); dogs (canine); cattle (bovine); sheep (ovine); pigs (porcine); llamas; and camels, for example.

Methods for Identifying and Characterizing UT Inhibitors

Methods that may be used to identify and to characterize urea transporter inhibitors, such as the compounds described herein, include red blood cell lysis methods and a stopped flow light scattering methods. Such assays may be used to determine the effective concentrations of a particular compound and thus are useful for predicting the capability of the compound to effectively treat a disease, disorder, or condition related to aberrant urea transporter activity in a subject.

One method for identifying and characterizing phenylsulfoxyoxazole, phenylsulfoxyimidazole, and phenylsulfoxythiazole compounds that are capable of inhibiting a urea transporter includes a cell lysis assay (see Example 1). The cell lysis assay is useful for determining the capability of a compound to alter transport of urea (or an analogue thereof) by a urea transporter, thus altering urea permeability of the cell. In particular embodiments, the method is useful for identifying and characterizing a compound having a structure (I) or a substructure described herein that inhibits (i.e., blocks, prevents, reduces, or decreases in a statistically or biologically significant manner) the capability of a urea transporter to transport urea across a cell membrane and thus inhibits urea influx and/or efflux. A compound that inhibits the capability of a urea transporter to transport urea may bind to the urea transporter such that transport of urea into the cell from the extracellular space is inhibited, or the compound may bind to the urea transporter such that transport of urea out of the cell into the extracellular space is inhibited or may inhibit both influx and efflux of urea.

A method for identifying an agent that inhibits transport of urea across a cell membrane (or influx or efflux of urea) comprises preparing a mixture, suspension, or sample of a plurality of indicator cells (which are obtained from or derived from a biological sample) and a hyperosmolar solution to obtain a mixture, suspension, or sample of the indicator cells in hyperosmolar conditions. The hyperosmolar solution includes a physiological solvent that is an appropriate diluent or media for cells and includes urea or a urea analog (including but not limited to formamide, acetamide, propionamide, N-methylurea, butyramide, and isobutyramide) at a concentration sufficient to result in a decrease in volume of an indicator cell due to flow of water out of the cell (efflux) when the indicator cells are placed into or incubated in the hyperosmolar solution.

Urea may be used as the solute in the hyperosmolar solution. The concentration of urea in a hyperosmolar solution may be any concentration between about 2.0-3.0 M or in certain other embodiments between about 1.5-3.0 M, or between about 2.3-2.7 M. In another embodiment, the hyperosmolar solution comprises a urea analogue, which may be at a concentration of about 1.25 M or may be any concentration between about 1.0-1.5 M, or between about 0.5-2.0 M or between about 1.0-1.75 M.

The concentration of urea or a urea analogue may be optimized by titration experiments so that an agent that inhibits transport of urea by a urea transporter is readily distinguished (i.e., quantifiably distinguishable) from the controls. For example, in a control sample that does not contain an agent or that contains an inactive agent, lysis of between 0%-40%, 0%-30%, 0%-20%, 0%-15%, or 0%-10% of the indicator cells (e.g., red blood cells) may be observed. In a sample that contains an inhibitor of a urea transporter, lysis of between 41%-100%, 50% to 100%, 60% to 100%, 70% to 100%, 80% to 100%, or 90% to 100% of indicator cells may be observed.

A hyperosmolar solution comprises a greater number of solute particles (osmoles) than a second different solution. Indicator cells are placed in a solution (i.e., the extracellular environment) made hyperosmolar by the presence of a particular solute, such that the concentration of the solute or solutes in the hyperosmolar solution is greater than the intracellular concentration of the solute(s). By placing the indicator cells in a hyperosmolar solution, water in the indicator cells will flow out of the cell, which in turn, results in the volume of the cell decreasing. Exemplary solutes include urea or a urea analog, for example, formamide, acetamide, propionamide, N-methylurea, butyramide, and isobutyramide. Exemplary indicator cells include red blood cells.

The indicator cells may be combined with the hyperosmolar solution in any of a variety of containers or sample vessels, including test tubes, multi-well plates such as 48-well, 72-well, 96-well, or 384-well plates, or other such vessels including those useful for high throughput screening formats wherein, for example, detection of indicator cell lysis in a plurality or reaction vessels may be automated. The cells may be in suspension or adhered to a surface. When cells are adherent cells, the surface to which the cells are adhered may be solid, such as a tissue culture plate (e.g., 24-well, 48-well, 72-well, 96-well plates, 384-well plate), or the cells may be adhered to microcarrier beads. Alternatively, the surface on which the cells adhere may be porous such that the apical cell surface and basolateral cell surface may be exposed to or bathed in the solutions described herein. The number of samples to be assayed may influence the degree of automation that can be implemented. For example, when high throughput screening, (i.e., assaying a large number of samples in a relatively brief time period) is desired, robotic or semi-robotic instruments may be used. In certain instances, microfluidics multiplexing technologies may be employed (see, e.g., Thorsen et al., Science 298:580-84 (2002); Manz and Becker, eds. *Microsystem Technology in Chemistry and Life Sciences* (Springer 1999); Zhang et al, *Microelectrofluidic Systems: Modeling and Simulation* (CRC Press 2002); Tabeling, *Introduction to Microfluidics* (Oxford University Press 2006)). Alternatively, samples may be processed manually, even for formats that accommodate large sample numbers (e.g., 96-well microplates).

Each vessel, tube, or well (herein referred to as sample) of indicator cells is maintained in (i.e., exposed to, placed in or incubated in) the hyperosmolar solution under conditions and for a time sufficient for the volume of the cell to decrease due to the directional flow of water out of the cell. Appropriate conditions for maintaining or incubating the indicator cells in a hyperosmolar solution include, for example, temperature; agitation and speed of agitation or other methods of maintaining the cells in suspension if the cells are suspension cells (that is, cells that are not adhered to a vessel, container, or multi-well plate); atmosphere (for example, the indicator cells may be a cell that requires an atmosphere containing carbon dioxide at a level typical for maintaining viability of cultured cells); and other conditions with which a person skilled in the art will be familiar.

The conditions and the period of time that the indicator cells are incubated in the hyperosmolar solution can be determined empirically for the type of indicator cell that is used. The temperature at which the cells may be incubated in the hyperosmolar solution may be a temperature or a range of temperatures considered ambient room temperature (e.g., between approximately 19° C.-26° C. or between approximately 21° C.-25° C.) or may be a temperature or range of temperatures considered physiological for animal cells (e.g., 37° C. or any temperature between 35° to 40° C.). Generally, the cells are placed in a hyperosmolar solution for at least 15 minutes, at least 30 minutes, at least 60 minutes (1 hour), at least 90 minutes, or at least 120 minutes (2 hours), or at least 180 minutes (3 hours), or at least 240 minutes (4 hours), or longer than 4 hours. By way of example, if the indicator cells are red blood cells, the cells may be placed in the hyperosmolar solution for 30 minutes to 120 minutes.

To each sample that is a mixture of indicator cells in a hyperosmolar solution is added at least one compound. In certain instances, such as screening a library with thousands of compounds, at least two, three, four, or more compounds may be added to the mixture. The mixture of indicator cells and the candidate agent are combined under conditions and for a time sufficient for the candidate agent to interact with the indicator cell, and particularly to interact with a urea transporter of the indicator cell. Persons skilled in the art will appreciate that appropriate conditions to permit interaction between the compound and the indicator cell include temperature; agitation and speed of agitation or other methods of maintaining contact between the indicator cells and the candidate agent; and atmosphere. The kinetics of binding of a transporter and an agent that alters the capability of a solute transporter to transport the solute may be rapid. Thus, in certain instances, the time sufficient for an indicator cell and candidate agent to interact may be 1-2 minutes, 3-4 minutes, 5-6 minutes, 7-8 minutes, or 9-10 minutes. In other instances, the time sufficient may be at least 10, 15, 20, 25, or 30 minutes or longer than 30 minutes.

After a sufficient time for the indicator cell and the candidate agent to interact, the osmolarity of the sample is decreased to place the indicator cells in a substantially isosmolar solution. The osmolarity of the sample may be reduced by removing the hyperosmolar solution and replacing the hyperosmolar solution with a second solution (e.g., a physiological buffer, diluent, or media) that lacks urea, or an analogue thereof, or that has a significantly reduced number of osmoles of the solute compared with the hyperosmolar solution, such that a mixture, suspension, or sample of the indicator cells in an isosmolar solution is obtained. Alternatively, the hyperosmolar mixture, combination, or sample of the indicator cells (in the absence and presence of the candidate agent) is diluted into a second solution (e.g., a physiological buffer, diluent, or media) to obtain a substantially isosmolar mixture. The percent dilution or fold-dilution of the hyperosmolar solution to provide a substantially isosmolar mixture may also be determined empirically for a particular type of indicator cell, and is the fold-dilution sufficient to observe an increase in the volume of the indicator cell as water flows into the cell. The osmoles in a substantially isosmolar mixture may be reduced at least ten fold compared with the osmoles of the hyperosmolar solution. For example, if the hyperosmolar is 1500 mOsm, the substantially isosmolar mixture may be about 150 mOsm. In certain embodiments, the osmoles in a substantially isosmolar mixture may be reduced between seven, eight, nine, or ten fold compared with the osmoles in the hyperosmolar solution. In other certain embodiments, the osmoles in a substantially isosmolar mixture may be reduced 11-12-, 13-, 14-, 15-, 16-, 17-, 18-, 19-, 20-fold or greater compared with the osmoles in the hyperosmolar solution.

To determine whether the presence of the compound in the sample inhibits urea transport by a urea transporter, the level of indicator cell lysis in the substantially isosmolar solution is determined. The level of lysis (partial or complete, as described herein) in indicator cells (e.g., red blood cells) in the presence of an agent (i.e., also referred to herein as a first level of lysis) that is an inhibitor of a urea transporter, is greater than the level of lysis in indicator cells that are not exposed to an inhibitor of the urea transporter (i.e., also referred to herein as a second level of indicator cell lysis). When the indicator cells in the hyperosmolar mixture comprising an active agent are transferred to, exposed to, resuspended in, placed in, or diluted into a substantially isosmolar solution, the indicator cells are incapable of transporting the solute out of the cell, thus entry of water into cells from the extracellular environment results in partial or total cell lysis. For example, in a sample that does not contain an agent or that contains an inactive agent, lysis between 0%-40%, 0%-30%, 0%-20%, 0%-15%, or 0%-10% of the indicator cells may be observed. In a sample that contains an inhibitor of a transporter, lysis of between 41%-100%, 50%-100%, 60%-100%, 70%-100%, 80%-100%, or 90%-100% of the indicator cells may be observed.

Lysis as used herein refers to complete or total lysis of a cell (i.e., complete and total disruption or loss of outer cell membrane integrity) or partial lysis of the cell (i.e., partial or incomplete disruption of the outer cell membrane integrity). The loss of integrity of the outer cell membrane, whether partial or complete, can be quantified using techniques practiced in the art and described herein. Release of an intracellular molecule may be detected by methods that detect the specific molecule, such as by an immunoassay, or by detecting a particular property or function of the intracellular molecule, for example, by measuring an enzymatic activity. Release of a cytoplasmic polypeptide or other molecule means that a polypeptide or other cellular molecule that is typically intracellular, that is, located in the cytoplasm of the cell or in an organelle of the cell but not secreted under normal physiological conditions when the cell is viable and intact, can be detected extracellularly.

Accordingly, methods and techniques that may be used to determine the level of cell lysis include any number of immunoassay methods (e.g., ELISA, radioimmunoassay, immunoprecipitation) for detecting release of a cytoplasmic polypeptide or other molecule from the cell. Release of a specific intracellular molecule or release of multiple intracellular molecules may be detected by detectably labeling the cells with a detectable moiety prior to placing the cells in the hyperosmolar solution. Exemplary detectable moieties (which may also be called tags, reporter molecules, or labels) include a dye, radionuclide, luminescent group, fluorescent group, or biotin, or the like. Methods for labeling cells with a reporter molecule and for detecting the reporter molecule are known to and routinely practiced by persons skilled in the art. Cell lysis may also be determined by techniques that detect the enzymatic activity of a specific intracellular enzyme. Other methods and techniques for determining the level of cell lysis include detecting a released intracellular molecule or molecules by methods that include mass spectrometry, chromatography (e.g., affinity chromatography wherein a ligand of an intracellular molecule is attached to a chromatography matrix), and spectrophotometry.

Spectrophotometric measurements may be determined at a wavelength in the visible or ultraviolet spectrum. The level of lysis of indicator cells, such as lysis of red blood cells, can be quantified by determining the absorbance at 710 nm of a sample (Mazeron et al. *Photochem. Photobiol.* 72:172-78 (2000); Cohn et al., *Mol. Biochem. Parasitol.* 132:27-34 (2003)). A sample that contains an inhibitor of a solute transporter, which has an increased level of cell lysis compared to a sample that does not contain a solute transporter inhibitor, exhibits a decreased level of absorbance at 710 nm compared with a control sample (i.e., in the absence of an inhibitor).

Other techniques for quantifying lysis of cells may be specific for one or more different types of indicator cells. For example, when the indictor cells are red blood cells, cell lysis may be quantified by quantifying hemoglobin, which may be accomplished spectrophotometrically, by chemical methods, or by any number of immunoassays practiced in the art. Additional exemplary methods for detecting red blood cell lysis include quantifying ATP that is released by the cell (Moehlenbrock et al., *Analyst* 131:930-7 (2006); Epub Jun. 6, 2006)); determining the level of cytoplasmic lactate dehydrogenase released, which can be measured in an enzymatic assay or in any number of immunoassays using an antibody that specifically binds to lactate dehydrogenase; or determining the level of oxygen released.

To determine whether an agent alters the volume of the indicator cell, the level of cell lysis of indicator cells that are contacted with a candidate agent (herein also called a first level of cell lysis) is compared with the level of lysis of indicator cells in the control sample that lacks the candidate agent (herein also called a second level of cell lysis). A control sample may be prepared in which all assay conditions and components are identical to those described above except that the candidate agent is omitted from the sample (i.e., indicator cells have not been contacted or combined with a candidate agent). Alternatively or in addition to such a control sample, at least one other control sample may include all the components of a sample that includes the candidate agent but instead of the candidate agent, the sample contains a compound or molecule that is known not to alter the volume of a cell. A person skilled in the art will also appreciate that the methods described herein may include additional control samples (including a sample comprising a known compound or agent that is capable of altering the volume of a cell) to evaluate and ensure the robustness, accuracy, and precision of the method. A person skilled in the art will also appreciate that the methods described herein may include additional control samples (including a compound or agent that is capable of inhibiting urea transport by a UT of the cell) to evaluate and ensure the robustness, accuracy, and precision of the method. Statistical methods may be applied to the determinations of cell lysis in the absence and presence of a candidate agent to evaluate and compare the different candidate agents tested.

As described herein, indicator cells used in the methods for identifying and characterizing the compounds described herein that inhibit transport of urea by a urea transporter may include cells that endogenously express at least one urea transporter or that recombinantly express at least one urea transporter. In certain instances, the indicator cells are red blood cells that endogenously express the UT-B urea transporter. The red blood cells may be obtained from any animal, including human and non-human primates, rodents (e.g., rats and mice), and other mammals. The solute of the hyperosmolar solution and the optimal concentration of the solute (i.e., urea or a urea analogue), may vary depending on the source of the indicator cell, which may be readily determined using the methods described herein. For example, when the indicator cell is a human red blood cell, the hyperosmolar solution may contain a urea analogue, such as acetamide. Alternatively, the red blood cells are obtained from a rodent such as a mouse and the urea analogue N-methylurea is the solute comprising the hyperosmolar solution.

The compounds having structure (I) or any substructure thereof (e.g., (Ia)-(Ij)) described herein that alter urea transport by a urea transporter may be analyzed and further characterized by additional methods and techniques described herein and practiced in the art. Such methods may be used in dose-response experiments to evaluate the effective concentration of each compound. Dose response experiments may be performed using the indicator cell lysis methods described herein. For example, the $EC_{50}$ (i.e., the concentration of a compound where 50% of its maximal effect is observed) of a solute transporter may be calculated by non-linear regression to the equation: % lysis=% $lysis_{min}$+(% $lysis_{max}[inh]^H$)/($EC_{50}{}^H$+$[inh]^H$), where [inh] is inhibitor concentration and H is the Hill coefficient.

Other methods for characterizing compounds include stopped-flow light scattering to measure solute and water permeabilities of a cell (see, e.g., Yang et al., *J Biol. Chem.* 277:36782-86 (2002; Epub 2002 Jul. 19); Macey et al., *J. Membr. Biol.* 134(3):241-50 (1993)). For example, to determine the urea permeability of a cell, dilutions of indicator cells, such as red blood cells, may be incubated with an agent and then subjected to an inwardly directed gradient of urea. After the cells osmotically shrink (i.e., the cell volume decreases), the kinetics of increasing cell volume caused by urea influx can be measured over a time course during which the cells are exposed to 90° scattered light intensity at 530 nm. As the volume of the cell increases, scattered light intensity is reduced. Stopped flow light scattering may also be used to determine $EC_{50}$ values for inhibition by a urea transporter and may also be used to determine the sideness of the inhibitor action (i.e., whether the inhibitor alters a solute transporter activity by preventing or inhibiting entry of a solute into the cell or whether the inhibitor alters a solute transport activity by preventing or inhibiting efflux of the inhibitor from the cell).

Thus, the compounds having the structure (I) and substructures described herein may be used to alter (i.e., increase or decrease in a statistically significant or biologically significant manner) a transporter activity of urea by at least one urea transporter. In particular embodiments, the transporter activity of a urea transporter is inhibited, thus the compounds are capable of preventing, blocking, or decreasing transport of urea across a cell membrane. Methods are provided for an in vitro assay in which a cell comprising at least one urea transporter is contacted (combined, mixed, or in some manner permitted to interact) with a composition comprising at least one compound described herein. In one embodiment, at least one compound described herein inhibits urea transport by the UT-B transporter. In another embodiment, at least one compound described herein inhibits the capability of a UT-A transporter to transport urea. In particular embodiments, the UT-A transporter is at least one of UT-A1, UT-A2, UT-A3, UT-A4, and UT-A5. In certain embodiments, the cell is a renal cell, a brain cell, a red blood cell, or a testis cell. In a particular embodiment, the cell is a renal cell. In another particular embodiment, the cell is a red blood cell and the red blood cell comprises at least a UT-B transporter.

Agents identified by the methods described herein include agents that are capable of inhibiting transport of urea across a cell membrane, and inhibiting entry of urea into a cell and/or inhibiting efflux of urea out of the cell. Provided herein are compounds that are potent urea transporter inhibitors, which include inhibitors of UT-B. The exemplary compounds belong to chemical classes, including but not limited to, phenylsulfoxyoxazoles and phenylsulfoxyimidazoles, which had submicromolar $EC_{50}$ values in red blood cell lysis assays and in stopped flow light scattering assays.

Agents and compounds identified and characterized by the methods described herein may be used in pharmaceutical compositions for treating diseases and conditions related to aberrant solute or water transport. The compounds described herein may be used to treat or ameliorate conditions and diseases related to aberrant urea transport such as conditions related to aberrant renal urea clearance. Such diseases and conditions include cardiovascular disease (e.g., hypertension and congestive heart failure), syndrome of inappropriate antidiuretic hormone secretion (SIADH), cirrhosis, azotemia, acute renal failure, chronic renal insufficiency, fluid retention, and abnormal uresis.

The compounds having the structure (I) and substructures (Ia)-(Ij) described herein may also be used for developing animal models that mimic a urea transporter knock-out animal model. For example, by administering a UT-B inhibitor to an animal, thus creating a "UT-B chemical knock out" animal, the mechanism and activities of other urea transporters may be studied and analyzed. Similarly, chemical UT-A knock out animals may be made by administering an inhibitor of a UT-A transporter, or by administering an inhibitor specific for one UT-A isoform. Such models would also be useful for determining the specificity and selectivity of a urea transporter inhibitor (see, e.g., Klein et al., *J Am Soc Nephrol.* 15:1161-67 (2004)).

Treatment of Urea Clearance Disorders

A composition comprising at least one of the phenylsulfoxyoxazole, phenylsulfoxyimidazole, and phenylsulfoxythiazole compounds described herein may be used for treating a disease, disorder, or condition in a subject. In one embodiment, methods are provided for treating a disease, disorder, or condition that is associated with aberrant transport of a neutrally charged solute (e.g., urea) by administering compositions comprising at least one compound as described herein. A disease, condition, or disorder related to or associated with aberrant transport of a neutrally charged solute includes a fluid retention imbalance, for example, urea clearance insufficiency. In certain instances, the urea clearance insufficiency is a renal urea clearance insufficiency associated with an abnormality, disease, or dysfunction that occurs in the kidneys. The compounds having the structure (I) and substructures (Ia)-(Ij) described herein may be used to treat a cardiovascular, renal, or metabolic disease, disorder, or condition such as hypertension, congestive heart failure, syndrome of inappropriate antidiuretic hormone secretion (SIADH), cirrhosis, azotemia, acute renal failure, chronic renal insufficiency, fluid retention, and abnormal uresis.

In a particular embodiment, methods are provided for treating such a disease, disorder, or condition by inhibiting the capability of at least one urea transporter to transport urea. In one embodiment, at least one of the compounds described herein inhibits the capability of a UT-B transporter to transport urea. In another embodiment, at least one compound described herein inhibits the capability of a UT-A transporter to transport urea. In particular embodiments, the UT-A transporter is at least one of UT-A1, UT-A2, UT-A3, UT-A4, and UT-A5. A compound having the structure (I) or substructures (Ia)-(Ij) may be used as a type of diuretic, a "urearetic," that affects renal urea clearance mechanisms.

Methods are also provided for using the compounds described herein for treating a disease, disorder, or condition associated with or related to aberrant transport of a neutrally charged solute in a subject by administering to the subject in need thereof a pharmaceutical composition comprising at least one of the compounds having the structure and substructures described above. The disease, disorder, or condition that is related to aberrant urea transporter activity includes a disease, disorder, or condition that is caused by, in whole or in part, by aberrant urea transport and also includes a disease, disorder, or condition for which aberrant urea transporter activity is a sequelae of the disease, disorder, or condition. The disease, disorder, or condition that may be treated using the compounds and compositions described herein may be associated with a fluid retention imbalance such as urea clearance insufficiency. Urea is a by-product of protein metabolism that is formed in the liver. Because urea contains ammonia, which is toxic to an animal body, urea must be quickly filtered from the blood by the kidneys and excreted in the urine. Also as described herein, conservation of water in mammals depends significantly on the transport of urea, particularly in the kidney. Urea is generated as the major end product of hepatic nitrogen metabolism and is excreted primarily by the kidney. In a particular embodiment the disease, disorder, or condition associated with aberrant urea transport is renal urea clearance insufficiency.

In one embodiment, treating any one of the aforementioned diseases or conditions comprises inhibiting (i.e., preventing, decreasing, reducing, abrogating, or inhibiting in a statistically significant or biologically significant manner) the capability of at least one urea transporter to transport urea by administering a composition comprising any one or more of the compounds having the structure (I) or substructures (Ia)-(Ij). The compound may inhibit a UT-B transporter and/or may inhibit at least one UT-A transporter or isoform thereof (e.g., UT-A1, UT-A2, UT-A3, UT-A4, UT-A5). The subject, and thus the source of the urea transporter, may be a human or non-human mammal. Exemplary non-human mammals include non-human primates, rodents such as mice, rats, or rabbits; cats (feline); dogs (canine); cattle (bovine); sheep (ovine); pigs (porcine); llamas; and camels; other domestic or zoo animals.

To evaluate and to monitor the effectiveness of a phenylsulfoxyoxazole, phenylsulfoxyimidazole, or phenylsulfoxythiazole compound described herein to treat a disease, disorder, or condition, one of several clinical assay methods may be performed. To evaluate and to monitor the effectiveness of any one of the compounds described herein to treat a disease, disorder, or condition, one or more of several clinical assay methods may be performed that are familiar to a person skilled in the clinical art. For example, a clinical method called a urea clearance test may be performed. A blood sample is obtained from a subject to whom the compound is being administered so that the amount of urea in the bloodstream can be determined. In addition, a first urine sample is collected from the subject and at least one hour later, a second urine sample is collected. The amount of urea quantified in the urine indicates the amount of urea that is filtered, or cleared by the kidneys into the urine. Another clinical assay method measures urine osmolality (i.e., the amount of dissolved solute particles in the urine). Inability of the kidneys to concentrate the urine in response to restricted fluid intake, or to dilute the urine in response to increased fluid intake during osmolality testing may indicate decreased kidney function.

Urea is a by-product of protein metabolism and is formed in the liver. Urea is then filtered from the blood and excreted in the urine by the kidneys. The BUN (blood urea nitrogen) test measures the amount of nitrogen contained in the urea. High BUN levels may indicate kidney dysfunction, but because blood urea nitrogen is also affected by protein intake and liver function, the test is usually performed in conjunction with determination of blood creatinine, which is considered a more specific indicator of kidney function. Low clearance values for creatinine and urea indicate diminished ability of the kidneys to filter these waste products from the blood and excrete them in the urine. As clearance levels decrease, blood levels of creatinine and urea nitrogen increase. An abnormally elevated blood creatinine, a more specific and sensitive indicator of kidney disease than the BUN, is diagnostic of impaired kidney function.

As used herein, a subject may be any mammal, including a human, that may have or be afflicted with a disease, condition, or disorder described herein. A pharmaceutical composition may be a sterile aqueous or non-aqueous solution, suspension or emulsion, which additionally comprises at least one physiologically acceptable excipient (i.e., a physiologically and pharmaceutically suitable non-toxic and inactive material or ingredient that does not interfere with the activity of the active ingredient; an excipient also may be called a carrier). Such compositions may be in the form of a solid, liquid, or gas (aerosol). Alternatively, compositions described herein may be formulated as a lyophilizate, or compounds may be encapsulated within liposomes using technology known in the art. Pharmaceutical compositions may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

Any suitable excipient or carrier known to those of ordinary skill in the art for use in pharmaceutical compositions may be employed in the compositions described herein. Excipients for therapeutic use are well known, and are described, for example, in *Remington: The Science and Practice of Pharmacy* (Gennaro, 21$^{st}$ Ed. Mack Pub. Co., Easton, Pa. (2005)). In general, the type of excipient is selected based on the mode of administration. Pharmaceutical compositions may be formulated for any appropriate manner of administration, including, for example, topical, oral, nasal, intrathecal, rectal, vaginal, intraocular, subconjunctival, sublingual or parenteral administration, including subcutaneous, intravenous, intramuscular, intrasternal, intracavernous, intrameatal or intraurethral injection or infusion. For parenteral administration, the carrier preferably comprises water, saline, alcohol, a fat, a wax or a buffer. For oral administration, any of the above excipients or a solid excipient or carrier, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose and/or magnesium carbonate, may be employed.

A pharmaceutical composition (e.g., for oral administration or delivery by injection) may be in the form of a liquid. A liquid pharmaceutical composition may include, for example, one or more of the following: a sterile diluent such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

A composition comprising a phenylsulfoxyoxazole, phenylsulfoxyimidazole, or phenylsulfoxythiazole compound described herein may be formulated for sustained or slow release. Such compositions may generally be prepared using well known technology and administered by, for example, oral, rectal or subcutaneous implantation, or by implantation at the desired target site. Sustained-release formulations may contain an agent dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

The dose of the composition for treating a disease or disorder associated with a fluid retention imbalance such as urea clearance insufficiency or for treating cardiovascular diseases (such as hypertension or congestive heart failure), syndrome of inappropriate antidiuretic hormone secretion (SIADH), cirrhosis, azotemia, acute renal failure, chronic renal insufficiency, fluid retention, and abnormal uresis may be determined according to parameters understood by a person skilled in the medical art. Accordingly, the appropriate dose may depend upon the subject's condition, that is, stage of the disease, general health status, as well as age, gender, and weight, and other factors considered by a person skilled in the medical art.

Pharmaceutical compositions may be administered in a manner appropriate to the disease to be treated as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity).

Optimal doses may generally be determined using experimental models and/or clinical trials. The optimal dose may depend upon the body mass, weight, or blood volume of the subject. In general, the amount of a phenylsulfoxyoxazole, phenylsulfoxyimidazole, or phenylsulfoxythiazole compound as described herein, that is present in a dose, ranges from about 0.01 µg to about 1000 µg per kg of host. The use of the minimum dose that is sufficient to provide effective therapy is usually preferred. Subjects may generally be monitored for therapeutic effectiveness using assays suitable for the condition being treated or prevented, which assays will be familiar to those having ordinary skill in the art and are described herein.

The following Examples are offered for the purpose of illustrating the present invention and are not to be construed to limit the scope of this invention.

EXAMPLES

Example 1

Red Blood Cell (RBC) Lysis Assay

An RBC lysis assay was developed in an automated, 96-well format high throughput format and optimized for identification and characterization of small-molecule UT-B inhibitors. Inhibition of UT-B mediated transport of urea by compounds was indicated by increased RBC lysis when urea- or acetamide-loaded RBCs were rapidly diluted into PBS (see FIG. 1). Conditions were optimized to give a robust assay for high-throughput screening that exhibited high sensitivity and a low false-positive rate. Absorbance at 710 nm was measured as a read-out of RBC lysis to minimize interference by test compounds and hemoglobin.

Screening of compounds for UT-B inhibitory activity in the RBC lysis assay was performed using a BECKMAN COULTER (Fullerton, Calif.) integrated system that included a 3-meter robotic arm, microplate carousel, liquid handling work station with parallel 96-well solution mixing and transfer (BIOMEK FX), plate sealer, and two fluorescence plate readers (FLUOstar Optima; BMG LABTECH Gmbh; Durham, N.C.), each equipped with a 710±5 nm absorption filter (CHROMA, Rockingham, Vt.). Chemicals were purchased from SIGMA-ALDRICH (St. Louis, Mo.) unless otherwise noted.

Mouse and Human Blood Collection

Human venous blood obtained from a single donor was collected into VACUTAINERS coated with sodium heparin (BECTON-DICKINSON, Franklin Lakes, N.J.), stored at 4° C., and used within 48 hr of collection. All human procedures were approved by the University of California, San Francisco Committee on Human Research. Whole mouse blood was collected from 8-12 week-old (25-35 g) wild-type; AQP1-null (Ma et al., *J Biol. Chem.* 273:4296-99 (1998)); or UT-B-null (Yang et al., *J Biol. Chem.* 277:10633-37 (2002)) mice in a CD1 genetic background by orbital puncture following subcutaneous injection with sodium heparin (150 USP units). All animal protocols were approved by the University of California, San Francisco Committee on Animal Research.

Assay Development

Inhibition of UT-B mediated transport of urea by compounds was indicated by increased RBC lysis when urea- or acetamide-loaded RBCs were rapidly diluted into PBS (see FIG. 1). Conditions were optimized to give a robust assay for high-throughput screening that exhibited high sensitivity and a low false-positive rate. Absorbance at 710 nm was measured as a read-out of RBC lysis to minimize interference by test compounds and hemoglobin. Urea and a panel of small urea-like solutes (e.g., formamide, N-methylurea, acetamide, propionamide, butyramide, and isobutyramide) were evaluated as the loading solute based on their transport kinetics and passage through UT-B. Acetamide was selected because its equilibration in RBCs was approximately 2-fold slower than water, which is optimal in an osmotic lysis assay, and because greater than 95% of its transport in RBCs is UT-B-dependent as determined by stopped-flow light scattering.

Figure 2:
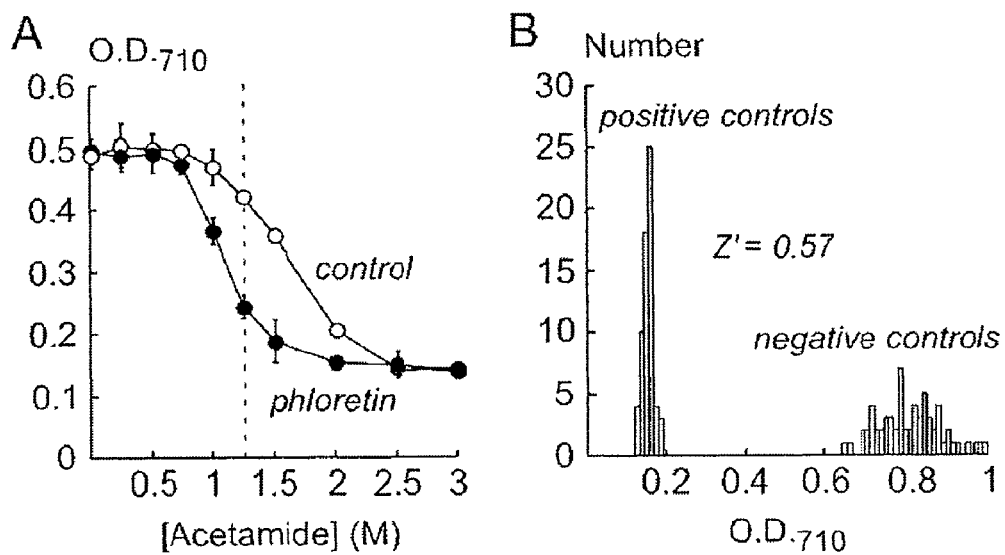
FIG. 2(A-B) presents graphs illustrating the red blood cell lysis assay.

The acetamide loading concentration that is optimal for identifying UT-B inhibitors was determined. FIG. 2A shows RBC lysis, determined by absorbance at 710 nm ($O.D._{710}$), as a function of the acetamide concentration used to load RBCs prior to mixing with acetamide-free buffer. Greater lysis, which is indicated by reduced $O.D._{710}$, was observed with increasing acetamide concentration. Fifty percent lysis was observed at approximately 1.6 M acetamide under control conditions (open circles) and at approximately 1.1 M when UT-B-facilitated acetamide transport was inhibited by phloretin (filled circles). To distinguish between control vs. inhibited UT-B, a concentration of 1.25 M acetamide (dashed vertical line) was chosen for the assay. Other technical considerations that were addressed during assay optimization included maintenance of RBC viability and uniform suspension, mixing conditions (rates, volumes and pipette tip locations in wells) and incubation time/temperature. The goodness of the optimized assay was evaluated by screening a series of plates containing positive and negative controls (100% and 0% lysis, respectively), which gave a very good statistical z'-factor of 0.57 for the screen (see FIG. 2B).

Example 2

High Throughput Screening of Small Molecule Libraries for UT-B Inhibitors

A primary screening for UT-B inhibitors was performed using a collection of 50,000 diverse, drug-like compounds (>90% with molecular size of 250-500 Da) obtained from a commercial source (CHEMDIV Inc., San Diego, Calif.). 96-well plates containing four compounds per well (each at 2.5 mM) were prepared for screening and then stored frozen in DMSO until use. Plates containing one compound per well (at 10 mM in DMSO) were stored separately and used later to identify and characterize individual active compounds.

Whole human blood was collected (see Example 1) and then prior to performance of the assay was diluted to a hematocrit of 1% in hyperosmolar PBS containing 1.25 M acetamide and 5 mM glucose (1550 mOsm, measured using freezing point-depression osmometry; PRECISION SYSTEMS, Natick, Mass.). Identical assay results were obtained when washed/centrifuged RBCs were used instead of whole blood. RBC suspensions were maintained at room temperature for up to 2 hr by periodic pipette mixing. Ninety-nine µL from a reservoir containing the RBC suspension was added to each well of a 96-well round-bottom microplate (FALCON, BECTON DICKINSON), to which test compounds were added (1 µL, 25 µM final compound concentration, 1% final DMSO concentration). After 6 min incubation, 20 µL of the RBC suspension was added rapidly to each well of a 96-well black-walled plate (COSTAR, Corning, N.Y.) containing 180 µL isosmolar buffer (PBS containing 1% DMSO) in each well. Vigorous mixing was achieved by repeated pipetting.

RBC lysis was quantified from a single time-point measurement of absorbance at 710-nm wavelength (Mazeron et al., *Photochem. Photobiol.* 72:172-78 (2000); Cohn et al., *Mol. Biochem. Parasitol.* 132:27-34 (2003)) made within 5 min after hyposmolar shock. Absorbance values were stable for at least 1 hr. Each assay plate contained eight negative 'no-lysis' controls (isotonic buffer; PBS+1.25 M acetamide with 1% DMSO) and eight positive 'full-lysis' controls (distilled $H_2O$ with 1% DMSO) that were mixed with DMSO vehicle-treated blood.

The statistical z'-factor, indicating 'goodness of the assay,' (Oldenburg et al., eds. *Handbook of Drug Screening*, New York, N.Y.; Marcel Dekkar, Inc. 549-554 (2001)) was computed using data from test plates as defined by: $z'=1-3[(SD_{pos}+ SD_{neg})/(A_{pos}-A_{neg})]$, where $SD_i$ and $A_i$ are the standard deviations and mean absorbance values for positive (pos) and negative (neg) controls. The percentage of RBC lysis in each test well of a given plate was calculated using control values from the same plate as follows: % lysis=100% $(A_{neg}-A_{test})/(A_{neg}-A_{pos})$, where $A_{test}$ is the absorbance value from a test well. During assay optimization, some test wells were incubated with the non-specific UT-B inhibitor phloretin (0.7 mM, dissolved at 100× in DMSO stock solution) as an additional positive control.

Figure 3:
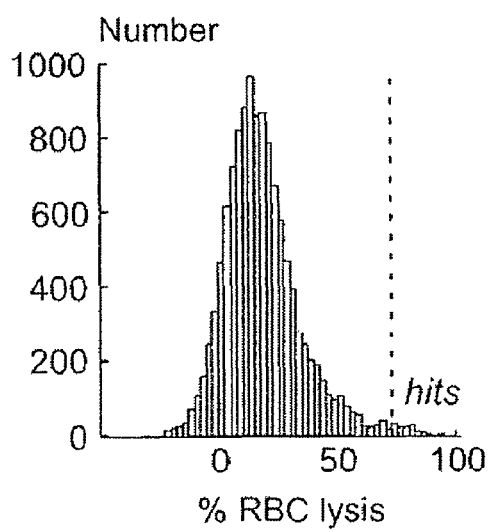
FIG. 3 presents a frequency histogram of percent erythrocyte lysis for a primary screen (12,500 test wells with 4 compounds per well; 50,000 compounds total). The dashed line representing the percent RBC lysis chosen to define 'hits.'

FIG. 3 shows the frequency histogram of $O.D._{710}$ values for all test compounds in the primary screen. Most compounds showed no significant apparent UT-B inhibition based on little (<30%) RBC lysis. Approximately 100 compounds producing greater than 75% lysis were selected for further evaluation.

Example 3

Stopped Flow Light Scattering Confirmatory Assay for Identification of UT-B Inhibitors RBC urea and water permeabilities were assayed by stopped-flow light scattering using a Hi-Tech Sf-51 instrument (Wiltshire, UK). For measurement of urea permeability, dilutions of whole blood (human or mouse; see Example 1) in PBS (hematocrit: approximately 0.5%) were incubated with test compounds for 5 min and then subjected to a 250-mM inwardly directed gradient of urea. After an initial osmotic shrinking phase, the kinetics of increasing cell volume caused by urea influx were measured as the time-course of 90° scattered light intensity at 530 nm, with increasing cell volume resulting in reduced scattered light intensity. As a positive control, 0.7 mM phloretin was added to the RBC suspension prior to stopped-flow experiments. Measurements of water permeability were carried out similarly, with sucrose (cell-impermeant) used instead of urea to establish a 250-mM osmotic gradient. As a positive control, $HgCl_2$ (0.3 mM) was added to the RBC suspension prior to stopped-flow measurements. Osmotic water permeability coefficients ($P_f$) were computed from light scattering data as described (van Hoek et al., *J Biol. Chem.* 267:18267-69 (1992)).

After repeating the 96-well plate RBC lysis assay to confirm compound activity (see Example 2), bona fide urea transport inhibition was determined by stopped-flow light scattering from the kinetics of urea influx (RBC swelling) in response to an inwardly directed urea gradient. Rapid mixing of an RBC suspension with a hyperosmolar solution containing excess 250 mM urea produced rapid cell shrinking due to osmotic water efflux, followed by cell swelling as urea (and water) influx occurred.

Figure 4:
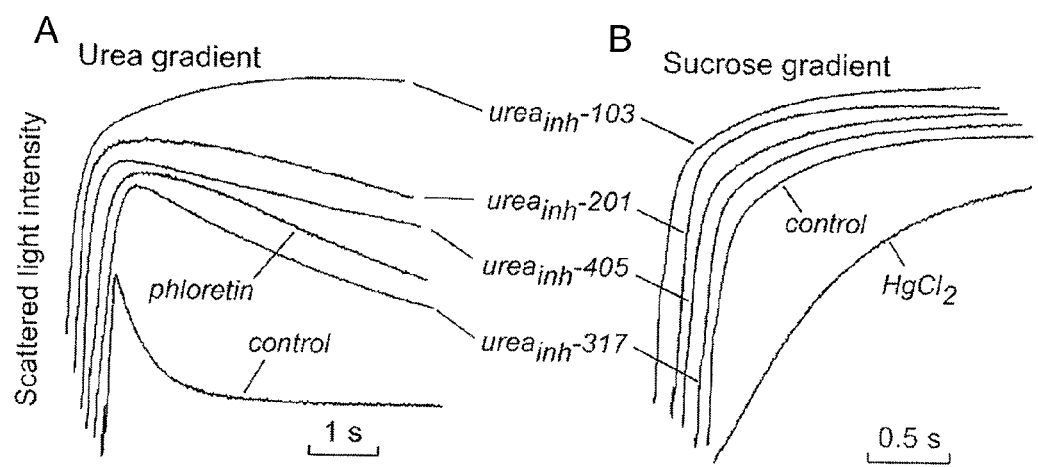
FIGS. 4A-B illustrate urea permeability measured by light scattering. (A) Urea permeability was measured from the kinetics of light scattering in response to a 250-mM inwardly directed urea gradient in the absence of inhibitor (control) or in the presence of 0.7 mM phloretin (positive control) or 5 μM of indicated compounds. (B) Osmotic water permeability of human RBCs was measured by light scattering in response to a 250-mM inwardly directed sucrose gradient in the absence or presence of 0.3 mM HgCl$_2$ (positive control) or 25 μM of each inhibitor.

Thirty-two compounds in four distinct chemical structural classes (phenylsulfoxyoxazole (and including phenylsulfoxyimidazoles), benzenesulfonanilide, phthalazinamine, and aminobenzimidazole) were identified that at 5 µM produced substantial inhibition (greater than 95%) of UT-B-facilitated urea transport. Other compounds, that exhibited either much lower or no activity in the stopped-flow assay, probably had apparent UT-B inhibitory activity in the primary screen in part due to RBC toxicity and consequent increased lysis. Original stopped-flow urea transport data for one representative compound (at 5 µM) of each class is shown in FIG. 4A. Tracings from control (no inhibitors) and phloretin-treated RBCs are provided for comparison. The new compounds at 5 µM inhibited UT-B-facilitated urea transport in human RBCs by greater than 95%, which was as good as or better than that with 0.7 mM phloretin. FIG. 4B shows that none of the UT-B inhibitors when tested at an even higher concentration of 25 µM, inhibited RBC osmotic water permeability as measured by cell shrinking in response to a sucrose gradient. Curves from negative control (no inhibitor) and positive control ($HgCl_2$ water transport inhibitor) are provided for comparison.

Example 4

Structure Activity Relationship Studies of UT-B Inhibitors

The activity of approximately 700 commercially available analogs (CHEMDIV Inc. and Asinex; Moscow, Russia) of active compounds from the four distinct chemical structural classes (phenylsulfoxyoxazole (and including phenylsulfoxyimidazoles), benzenesulfonanilide, phthalazinamine, and aminobenzimidazole) identified in the primary screen was determined to establish structure-activity relationships (SAR) and, potentially, to identify compounds with improved UT-B inhibitory potency. These compounds were tested against human and mouse UT-B using the RBC lysis assay. For some of the more active compounds, dose-response experiments were performed using human and/or mouse blood in the lysis assay. $EC_{50}$ was calculated by non-linear regression to the equation: % lysis=% $lysis_{min}$+(% $lysis_{max}$: $[inh]^H)/(EC_{50}{}^H+[inh]^H)$, where [inh] is inhibitor concentration and H is the Hill coefficient.

Figure 5:
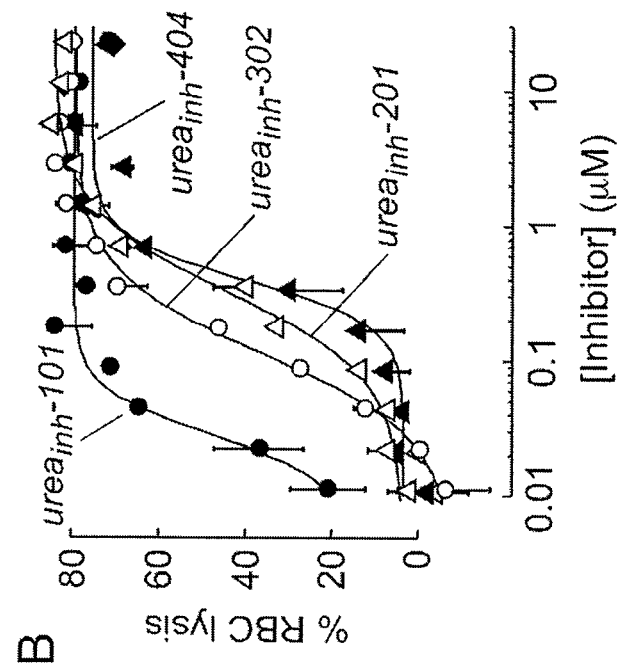
FIG. 5A presents the chemical structures of representative UT-B inhibitors (urea$_{inh}$), identified from primary high-throughput screening and assay of analogs.
FIG. 5B presents dose-inhibition data for the inhibitors shown in FIG. 5A determined by the lysis assay using human RBCs (±SD) and fit to calculate EC$_{50}$ (solid lines) as described in Example 4.
Figure 5:
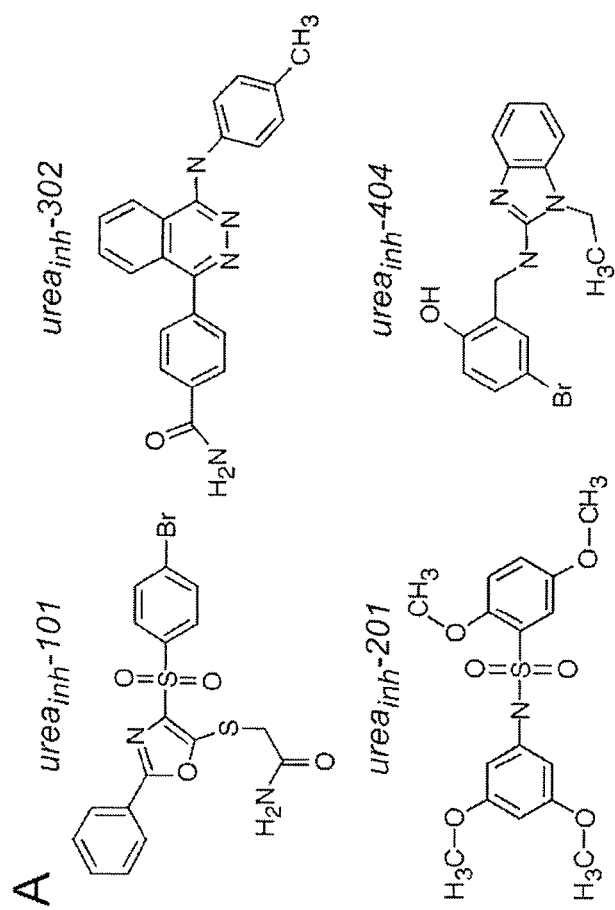

The analogs were screened at 25 µM. Concentration-inhibition data were obtained for those compounds producing greater than 75% apparent UT-B inhibition by the RBC lysis assay. FIG. 5A shows the chemical structures of potent compounds from each of the phenylsulfoxyoxazole, benzenesulfonanilide, phthalazinamine, and aminobenzimidazole classes. These structures are unrelated to either phloretin or urea analog inhibitors. FIG. 5B shows concentration-inhibition data with apparent $EC_{50}$ values (in nM) for exemplary compounds: $urea_{inh}$-101, 30 nM; $urea_{inh}$-201, 300 nM; $urea_{inh}$-302, 100 nM; and $urea_{inh}$-404, 400 nM.

Example 5

Determination of $EC_{50}$ of Urea Transport Inhibitors

To determine $EC_{50}$ values for urea transport inhibition directly, RBC urea transport was measured by stopped-flow light scattering using a non-saturating concentration of extracellular urea (to avoid possible competition effects). $EC_{50}$ for inhibition of RBC urea transport was determined independently by comparing stopped-flow light scattering curves to a model of cell shrinking-swelling.

For stopped-flow experiments, a 100-mM gradient of urea (for human RBCs) or N-methylurea (for mouse RBCs) was used to minimize competition effects (apparent urea and N-methylurea affinities at 23° C. are approximately 200 and approximately 100 mM, respectively) (Mayrand et al., *J Gen Physiol.* 81:221-37 (1983)). N-methylurea, with greater than 2-fold slower RBC permeability than urea, was used in mouse studies to better resolve overlapping water and urea transport kinetics. Dose-response data were also collected for human RBCs using a high concentration of 1 M urea to distinguish between competitive vs. non-competitive inhibitor binding.

The two coupled differential equations describing water efflux and solute influx in response to externally added urea or methylurea were numerically integrated using the forward Euler method ($\Delta t=0.01$ s) to reproduce the biphasic changes in cell volume observed experimentally. Computations that were performed using the smaller time step ($\Delta t=0.001$ s) gave similar results, confirming the adequacy of the 0.01 s time step. Water flux, $J_v$ (in cm$^3$/s), across erythrocyte membranes is represented by the following equation: $J_v = -P_f \cdot S \cdot v_w \cdot [(I_e - I_c(i)) + (U_e - U_c(i))]$; solute flux, $J_s$ (in mol/s), is represented by the following equation: $P_s \cdot S \cdot (U_e - U_c(i))$. Permeability coefficients ($P_f$ and $P_s$) are expressed in units of cm/s, cell surface area (S) in cm$^2$, extracellular (e) and cellular (c) concentrations of impermeant (I) and urea/methylurea (U) solute in mol/cm$^3$, and $v_w$ is 18 mol/cm$^3$. Initial conditions were $I_e = I_c(0) = 2.9 \times 10^{-4}$ mol/cm$^3$, $U_e = 10^{-4}$ mol/cm$^3$, and $U_c(0) = 0$. For each time step, a new cell volume (normalized to the initial size; $V(i+1)/V(0)$) and a new cell permeant concentration ($U(i+1)$) were calculated from $V(i+1)/V(0) = V(i)/V(0) - \Delta t \cdot P_f \cdot (S/V(0)) \cdot v_w \cdot [I_e(1 - V(i)/V(0)) + (U_e - U_c(i))]$ and $U_c(i+1) = U_c(i)/V(0) - \Delta t \cdot U_s \cdot (S/V(0)) \cdot v_w \cdot (U_e - U_c(i))$. Normalized cell volume was assumed to be inversely proportional to scattered light intensity. The product of $P_f$ and the surface area-to-volume ratio ($S/V(0)$) was determined to be $3.4 \times 10^2$ s$^{-1}$ and $8.5 \times 10^2$ s$^{-1}$ for human and mouse erythrocytes, respectively, from water permeability measurements. $P_s$ was varied to reproduce experimental data, and EC$_{50}$ was computed using non-linear regression (see above) of $P_s$ vs. [inh] data.

Figure 6:
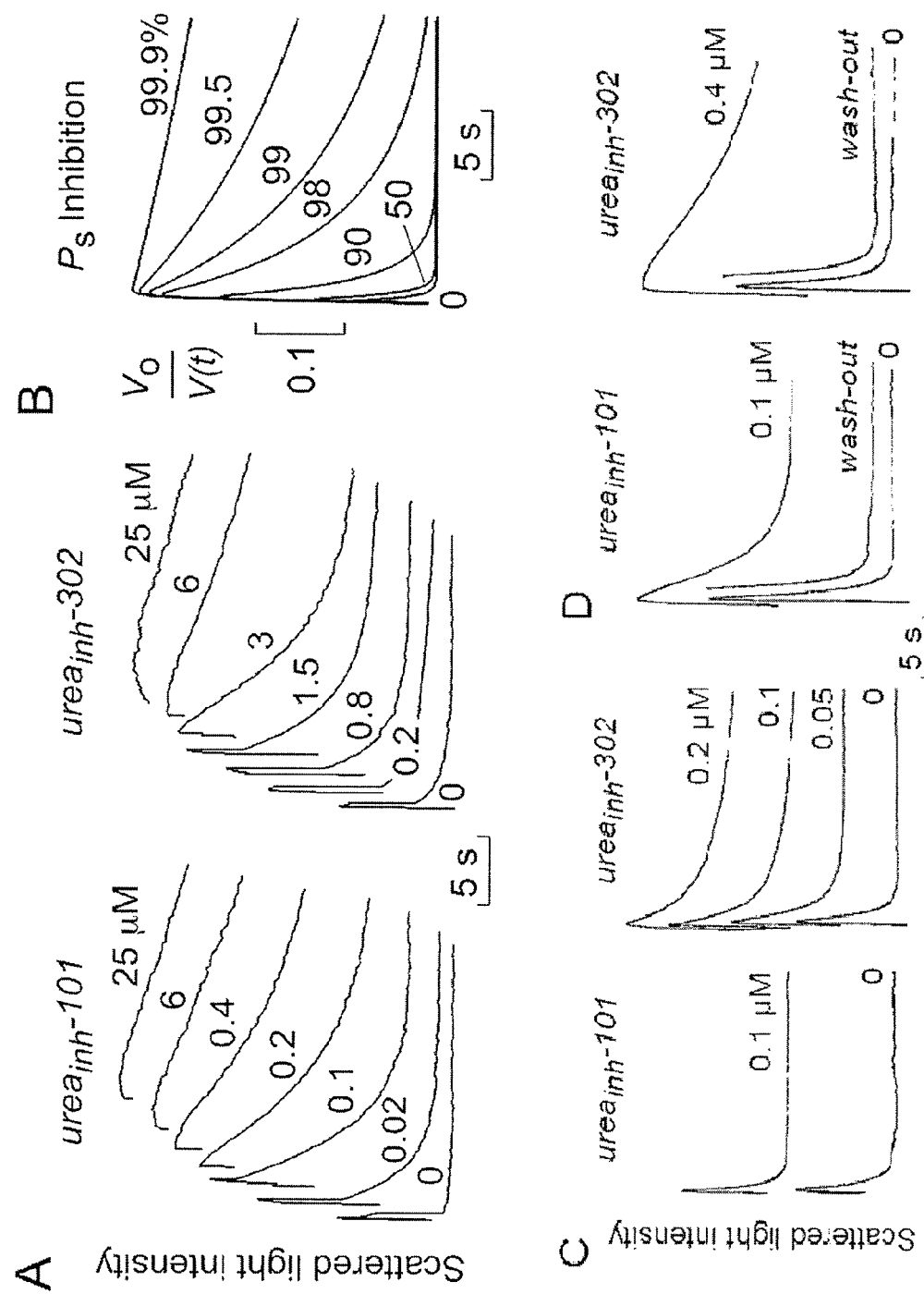
FIGS. 6A-D present stopped-flow measurements of urea transport in human RBCs.

FIG. 6A shows representative data for inhibition of RBC urea transport by the compounds designated urea$_{inh}$-101 and urea$_{inh}$-302. Urea permeability coefficients ($P_s$) were determined from light-scattering curves by numerical integration of the flux equations for coupled RBC water/urea transport as described above. An example of computed concentration-inhibition data is plotted in FIG. 6B. The deduced EC$_{50}$ values from stopped-flow measurements were in general agreement with the EC$_{50}$ values determined in the lysis assay. The computations indicated that 50% UT-B inhibition produces a subtle change (approximately 2-fold slowing) in the light-scattering curve, whereas the more obvious visual evidence for slowed kinetics is seen at >95% inhibition. These computations indicated that many of the inhibitors produced greater than 99% UT-B inhibition.

To determine the sidedness of inhibitor action, compounds were added only to the urea-containing solution (at concentrations 2 times higher than their EC$_{50}$) before mixing with RBCs in stopped-flow measurements. To assay for reversibility, compounds (at concentrations 4 times higher than their EC$_{50}$) were added to RBCs for 10 min and then washed by centrifugation prior to stopped-flow measurements.

RBCs were exposed externally to urea$_{inh}$-101 and urea$_{inh}$-302 at final concentrations of 0.1 and 0.2 µM, respectively (approximately 2 times their EC$_{50}$) just at the time of stopped-flow experiments (inhibitor inclusion only in urea-containing solution). Whereas urea$_{inh}$-101 did not inhibit urea transport under these conditions, suggesting an intracellular site of action, urea$_{inh}$-302 had a sizable effect (see FIG. 6C). The inhibition of urea permeability by externally added urea$_{inh}$-302 was concentration-dependent.

To test reversibility of inhibition, RBCs were pre-incubated with urea$_{inh}$-101 or urea$_{inh}$-302 for 10 min (at 0.1 and 0.4 µM, respectively), which resulted in greater than 95% transport inhibition. After the RBCs were washed, urea transport was identical to transport in RBCs that were not exposed to an inhibitor, indicating fully reversible inhibition (see FIG. 6D).

Example 6

Structure-Activity Analysis (SAR) of UT-B Inhibitors

UT-B inhibitory potencies for the most active compounds having the structure (I) are summarized in Table 1.

Class I Compounds: Phenylsulfoxyoxazoles and Phenylsulfoxyimidazoles

Compounds identified included many phenylsulfoxyoxazoles, but also included several phenylsulfoxyimidazoles (urea$_{inh}$-130-132) (see Table 1). In highly active compounds, unsubstituted thioglycoamide was present as R1 (urea$_{inh}$-101-119). Compounds with reduced activity often had amino groups such as mono/dialkylated amines (urea$_{inh}$-120-123), n-morpholino (urea$_{inh}$-124-125), and hexahydro-1-H-azepine-1-yl (urea$_{inh}$-126-128) as R1. Compounds that comprise R1 as a thioglycoamide of a mono- or dialkylated amide (e.g., SCH$_2$—CO—NHR or SCH$_2$—CO—NR$_2$) when R was a phenyl group or bulky aliphatic group were inactive. The compounds with the lowest EC$_{50}$ values (EC$_{50}$<100 nM) contained 2-thiophene or phenyl rings at R2. Compounds with 2-furan at R2 also exhibited submicromolar potency. Methyl (Me) or halo substitutions at the 4-position of the phenyl ring of R2 reduced activity, while compounds with 3-, di, or tri-substituted phenyl rings at R2 were inactive. For R3 substitutions, halo and methyl groups conferred substantially greater activity compared to unsubstituted analogs.

TABLE 1

Structure-Activity Analysis of Phenylsulfoxyoxazoles and Phenylsulfoxyimidazoles

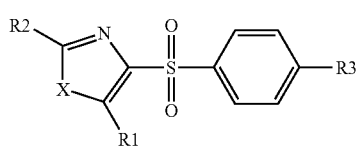

Class I: Phenylsulfoxyoxazoles and Phenylsulfoxyimidazoles

| Compound | X | —R1 | —R2 | —R3 | EC$_{50}$ (µM) |
|---|---|---|---|---|---|
| urea$_{inh}$-101* | O | —S—CH$_2$—CO—NH$_2$ | —Ph | —Br | 0.03 |
| urea$_{inh}$-102* | O | —S—CH$_2$—CO—NH$_2$ | —Ph | —Cl | 0.04 |
| urea$_{inh}$-103* | O | —S—CH$_2$—CO—NH$_2$ | —Ph | —Me | 0.1 |

TABLE 1-continued

Structure-Activity Analysis of Phenylsulfoxyoxazoles and Phenylsulfoxyimidazoles

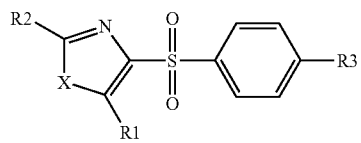

Class I: Phenylsulfoxyoxazoles and Phenylsulfoxyimidazoles

| Compound | X | —R1 | —R2 | —R3 | $EC_{50}$ (µM) |
|---|---|---|---|---|---|
| $urea_{inh}$-104* | O | —S—$CH_2$—CO—$NH_2$ | —Ph | —H | 1 |
| $urea_{inh}$-105* | O | —S—$CH_2$—CO—$NH_2$ | -(4-F)—Ph | —Me | 0.1 |
| $urea_{inh}$-106 | O | —S—$CH_2$—CO—$NH_2$ | -(4-F)—Ph | —Cl | 0.2 |
| $urea_{inh}$-107* | O | —S—$CH_2$—CO—$NH_2$ | -(4-F)—Ph | —F | 6 |
| $urea_{inh}$-108* | O | —S—$CH_2$—CO—$NH_2$ | -(4-F)—Ph | —H | 15 |
| $urea_{inh}$-109* | O | —S—$CH_2$—CO—$NH_2$ | -(4-Me)—Ph | —Br | 0.2 |
| $urea_{inh}$-110* | O | —S—$CH_2$—CO—$NH_2$ | -(4-Me)—Ph | —Me | 1 |
| $urea_{inh}$-111 | O | —S—$CH_2$—CO—$NH_2$ | -(4-Me)—Ph | —Cl | 1 |
| $urea_{inh}$-112 | O | —S—$CH_2$—CO—$NH_2$ | -(4-Me)—Ph | —H | 15 |
| $urea_{inh}$-113 | O | —S—$CH_2$—CO—$NH_2$ | -2-thiophene | —Cl | 0.02 |
| $urea_{inh}$-114* | O | —S—$CH_2$—CO—$NH_2$ | -2-thiophene | —Me | 0.5 |
| $urea_{inh}$-115 | O | —S—$CH_2$—CO—$NH_2$ | -2-thiophene | —F | 0.6 |
| $urea_{inh}$-116 | O | —S—$CH_2$—CO—$NH_2$ | -2-thiophene | —H | 1 |
| $urea_{inh}$-117* | O | —S—$CH_2$—CO—$NH_2$ | -2-furan | —Cl | 0.1 |
| $urea_{inh}$-118* | O | —S—$CH_2$—CO—$NH_2$ | -2-furan | —Br | 0.2 |
| $urea_{inh}$-119* | O | —S—$CH_2$—CO—$NH_2$ | -2-furan | —Me | 1 |
| $urea_{inh}$-120 | O | —NH—$CH_2$—Ph | -(2-F)—Ph | —Cl | 1 |
| $urea_{inh}$-121 | O | —S—$CH_2$—CO—NH—$CH_2$—2-furan | —Ph | —Br | 4 |
| $urea_{inh}$-122 | O | —S—$CH_2$—CO—NH—$CH_2$—2-furan | —Ph | —Cl | 15 |
| $urea_{inh}$-123 | O | —N($CH_3$)$_2$ | -(2-Cl)—Ph | —H | 5 |
| $urea_{inh}$-124 | O | -n-morpholino | -(2-F)—Ph | —H | 7 |
| $urea_{inh}$-125 | O | -n-morpholino | -(2-Cl)—Ph | —Me | 11 |
| $urea_{inh}$-126 | O | -hexahydro-1-H-azepine-1-yl | -(2-OMe)—Ph | —H | 10 |
| $urea_{inh}$-127 | O | -hexahydro-1-H-azepine-1-yl | -(4-Me)—Ph | —H | 10 |
| $urea_{inh}$-128 | O | -hexahydro-1-H-azepine-1-yl | -(4-F)—Ph | —H | 10 |
| $urea_{inh}$-129* | O | —SMe | -2-furan | —Cl | 20 |
| $urea_{inh}$-130* | N | —SMe | -(4-Me)—Ph | —H | 2 |
| $urea_{inh}$-131 | N | —SH | —Ph | —Me | 6 |
| $urea_{inh}$-132 | N | —S—CO—Ph | —Ph | —H | 7 |

Inactive compounds:
R1: $SCH_2$—CO—$NR_2$, $SCH_2$—CO—NHR (R is substituted Phenyl (Ph) or bulky aliphatic)
R2: 3-, di-, or tri-substituted phenyls
*Denotes inhibitors identified in primary screening

Example 7

Effect of UT-B Inhibitors on Rodent Urea Transport

To identify UT-B inhibitors that would be useful for studies in mouse models, the inhibitors of human UT-B were screened for activity against mouse UT-B in the RBC lysis assay, performed essentially as described in Example 1. Whereas many phenylsulfoxyoxazole compounds and phthalazinamine compounds that were highly active against human UT-B were active against mouse UT-B in the RBC lysis assay, none of the benzenesulfonanilide or aminobenzimidazole compounds were active against mouse UT-B in the RBC lysis assay at concentrations as high as 25 µM. The amino acid sequences of human UT-B and murine UT-B exhibit approximately 85% sequence identity (Yang et al., supra). Similar UT-B inhibitory potencies were measured in assays using mouse RBCs and in assays using rat RBCs, which was not unexpected in view of the closely related amino acid sequences of murine and rat UT-B.

Figure 7:
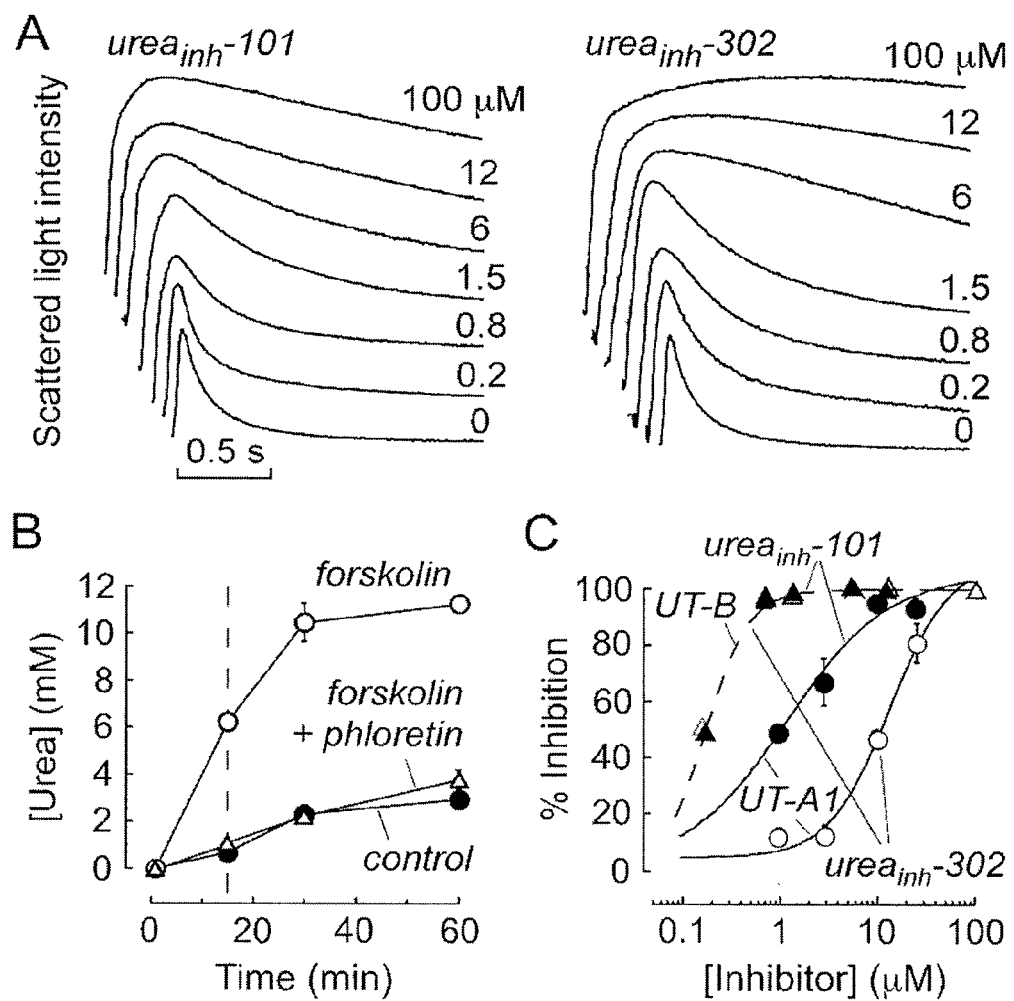
FIGS. 7A-C illustrate activity of UT-B inhibitors against rodent UT-B and UT-A1.

$EC_{50}$ values for the most potent compounds that exhibited activity in the mouse RBC lysis assay were determined by stopped-flow light scattering (see Example 3). Representative curves for two UT-B inhibitors ($urea_{inh}$-101 and $urea_{inh}$-302) are shown in FIG. 7A. For these studies using mouse RBCs, methylurea was used as the transported solute instead of urea because its transport is slower, allowing better estimation of $EC_{50}$ values. Concentration-inhibition data indicated that the most potent phenylsulfoxyoxazole compounds and phthalazinamine compounds had an $EC_{50}$ of approximately 200 nM for mouse UT-B. These compounds, when tested at 25 µM, did not affect urea transport in RBCs from UT-B-null mice.

Example 8

Effect of UT-B Inhibitors on UT-A Transporter

Concentration-inhibition studies were performed to study the effect of the active mouse UT-B inhibitors on urea transport by UT-A. The amino acid sequences of UT-B and UT-A urea transporter isoforms share significant similarity. The cells used in these studies were MDCK cells that expressed rat UT-A1. MDCK-UT-A1-expressing cells were grown on collagen-coated porous filters until they were electrically tight, at which point 15 mM urea was introduced into buffer bathing the basolateral cell surface.

MDCK cells stably transfected with rat UT-A1 (MDCK-UT-A1) (Fröhlich et al., Am J Physiol. in press; Fröhlich et al., Am. J. Physiol. Cell Physiol. 286:C1264-70 (2004). Epub on Jan. 28, 2004) were generously provided by Dr. Jeffrey Sands (Emory University School of Medicine, Atlanta, Ga.). Cells were grown in Dulbecco's Modified Eagle Medium (DMEM) with bicarbonate and supplemented with 10% fetal bovine serum (FBS), 25 mM HEPES buffer, penicillin G (100 U/mL), streptomycin (100 μg/mL) and hygromycin (500 μg/mL). For determining urea flux, cells were grown on 12-mm collagen-coated TRANSWELL inserts (0.4 μm pore size; COSTAR) as described (Fröhlich et al., *Am J Physiol.* in press; Fröhlich et al., 2004, supra). The TRANSWELL inserts were incubated in hygromycin-free medium for 1 hr in a 5% $CO_2$ tissue culture incubator (37° C.), and then $2 \times 10^5$ cells/cm² were loaded onto each insert. Cells were used after culturing the cells for 4 days in hygromycin-free medium, at which time they formed tight monolayers (transepithelial resistance 500-600 Ω·cm²).

UT-A1-facilitated urea flux in the basolateral-to-apical direction across unstimulated and forskolin-stimulated MDCK-UT-A1 cell layers was measured in response to a 15-mM urea gradient. Experiments were carried out in 12-well plates in which PBS, containing either DMSO vehicle or forskolin, with or without UT-B inhibitor, added to both the apical-facing (0.2 mL) and basal-facing (1 mL) surfaces of cells on the porous filters. Cultures were incubated in the absence of urea for 30 min at 37° C. Then, the basal-facing solution was replaced with PBS (containing same components) with 15 mM urea. Five μL samples of apical fluid were collected at specified times during incubation at 37° C., and urea concentration was determined using a commercial kit based on chromogenic urea complexation at 520-nm wavelength (Quantichrom™ Urea Assay Kit, BioAssay Systems, Hayward, Calif.). Forskolin (10 μM), with or without UT-B transport inhibitors, was added from 1000×DMSO stock solutions (0.2% final DMSO content). Inhibition of UT-A1-mediated transport was defined as % inhibition=100%·$(A_{forsk}-A_{test})/(A_{forsk}-A_{phlor})$. $A_{forsk}$ and $A_{phlor}$ were averaged absorbance values (at 520 nm) for cultures treated with forskolin and forskolin+phloretin, respectively, and $A_{test}$ were values from cultures treated with forskolin+test compound.

FIG. 7B illustrates the kinetics of urea appearance in the apical solution. UT-A1-facilitated urea transport was strongly increased by the cAMP agonist forskolin and inhibited by phloretin (Fröhlich et al., *Am J Physiol.* in press; Fröhlich et al., 2004, supra). Concentration-inhibition data were obtained at a 15-min time point when urea accumulation in the apical bathing solution is approximately linear. Urea$_{inh}$-101 was more active ($EC_{50}$ equaled approximately 1.2 μM) against rat UT-A1 than urea$_{inh}$-302 ($EC_{50}$ equaled approximately 15 μM) (FIG. 7C). For comparison, concentration-inhibition data are shown for mouse UT-B, which indicates selectivity of these compounds for UT-B over UT-A1. Neither urea$_{inh}$-201 at 25 μM nor urea$_{inh}$-404 at 25 μM significantly inhibited rat UT-A1.

Example 9

Effect of UT-B Inhibitors on UT-B-Facilitated Water Transport

Figure 8:
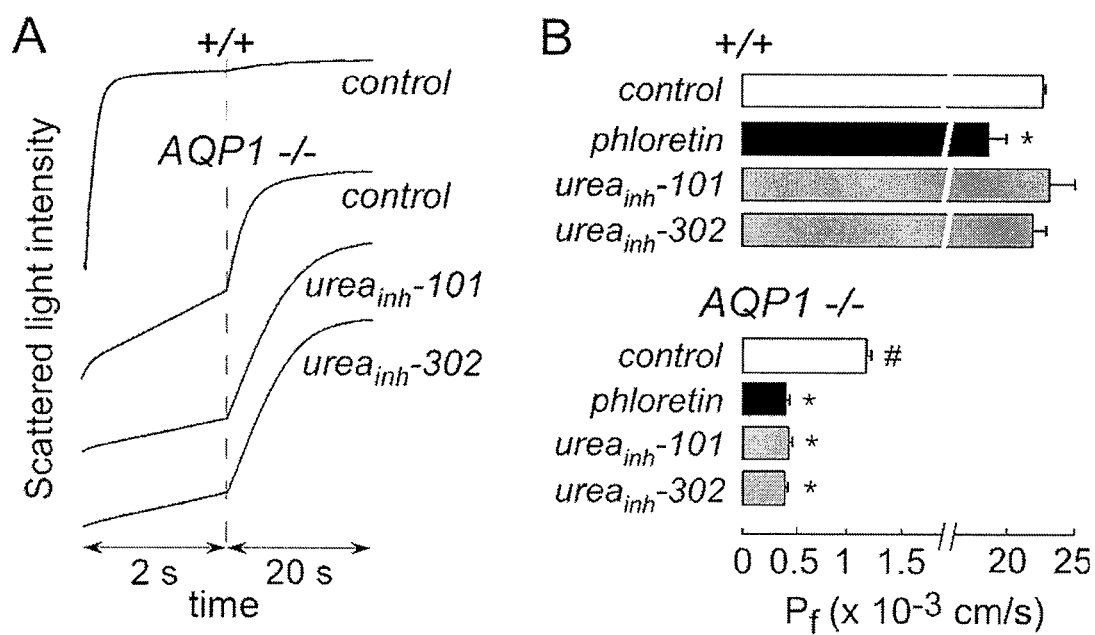
FIGS. 8A-B illustrate UT-B-facilitated water transport by 'chemical UT-B knock-out'. Osmotic water permeability was measured from the time course of RBC volume in response to a 250-mM inwardly directed sucrose gradient.

This example describes chemical knock-out of UT-B by UT-B inhibitors in RBCs and the effect on UT-B-facilitated water transport. Compounds, urea$_{inh}$-101 and urea$_{inh}$-302, which have good inhibitory potencies against mouse UT-B, were used to test the hypothesis that UT-B contains a pore that conducts water in response to an osmotic gradient. Osmotic water permeability was measured by stopped-flow light scattering in RBCs from wild-type and AQP1-null mice as shown in FIG. 8A. Water permeability coefficients are summarized in FIG. 8B. The UT-B inhibitors phloretin, urea$_{inh}$-101, and urea$_{inh}$-302 had little effect on water transport in RBCs from wild-type mice, as expected because AQP1 provides the principal route for water transport. Phloretin at 0.7 mM produced a small but significant reduction in $P_f$ that was likely due to its non-specific effects on membrane fluidity. AQP1-null RBCs had greater than 5-fold reduced $P_f$ compared to wild-type RBCs. As illustrated in FIG. 8B, urea$_{inh}$-101 and urea$_{inh}$-302 further inhibited water permeability in AQP1-null RBCs, indicating that UT-B-facilitated water transport occurs in the cells.

From the foregoing, although specific embodiments of the invention have been described herein for purposes of illustration, various modifications may be made without deviating from the spirit and scope of the invention. Those skilled in the art will recognize, or be able to ascertain, using no more than routine experimentation, many equivalents to the specific embodiments of the invention described herein. Such equivalents are intended to be encompassed by the following claims.

We claim the following:

1. A composition comprising a physiologically acceptable excipient and a compound having the following structure (I):

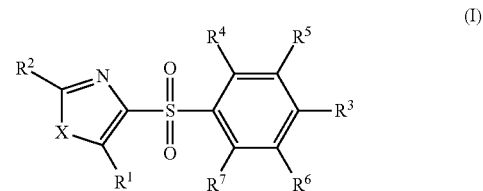

or a pharmaceutically acceptable salt, prodrug or stereoisomer thereof, wherein

X is $NR^8$, O, or S;

$R^1$ is $-S(CH_2)_nC(=O)NHR^{10}$ wherein n is 1 to 6 and $R^{10}$ is hydrogen, straight-chain $C_{1-6}$ alkyl, arylalkyl, or heterocycloalkyl;

$R^2$ is hydrogen, hydroxyl, halogen, alkyl, aryl, arylalkyl, arylalkylamino, heterocycle or heterocycloalkyl;

$R^3$, $R^4$, $R^5$, $R^6$ and $R^7$ are each the same or different and independently hydrogen, halogen or alkyl; and $R^8$ is hydrogen or alkyl.

2. The composition of claim 1 wherein at least two of $R^4$, $R^5$, $R^6$ and $R^7$ are hydrogen.

3. The composition of claim 1 wherein X is O or NH.

4. The composition of claim 1 wherein $R^2$ is aryl, alkoxyaryl, or 5-7-membered heterocycle having at least O or S.

5. The composition of claim 1 wherein $R^2$ is unsubstituted phenyl or phenyl substituted with halogen, $C_{1-6}$ alkyl, or $C_{1-6}$ alkoxy at a position meta or para to the linking carbon.

6. The composition of claim 1 wherein $R^2$ is unsubstituted phenyl; mono-substituted phenyl with fluoro, chloro, methyl, or methoxy at a position meta or para to the linking carbon; thiophene-2-yl; or furan-2-yl.

7. The composition of claim 1 wherein each of $R^4$, $R^5$, $R^6$ and $R^7$ is the same or different and independently hydrogen, or halogen, or $C_{1-6}$ alkyl.

8. The composition of claim 1 wherein each of $R^4$, $R^5$, $R^6$ and $R^7$ is hydrogen.

9. The composition of claim 1 wherein $R^3$ is hydrogen, halogen, or $C_{1-6}$ alkyl.

10. The composition of claim 1 wherein $R^3$ is hydrogen, halogen, or methyl.

11. The composition of claim 1 wherein X is O.

12. The composition of claim 1 wherein $R^1$ is
—S-(2-mercaptoacetamidyl);
—S—[N-(furan-2-yl-methyl)-2-mercaptoacetamidyl);
—S-mercaptomethyl;
sulfhydryl; or
—S-benzothioate.

13. The composition of claim 11 wherein $R^1$ is —S-(2-mercaptoacetamidyl) and the compound has the following substructure (Ia):

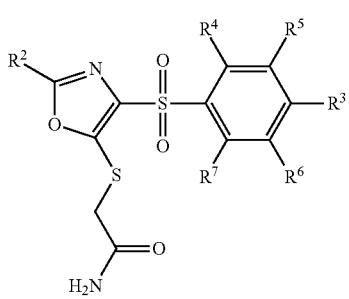

or a pharmaceutically acceptable salt, prodrug or stereoisomer thereof.

14. The composition of claim 13 wherein $R^2$ is unsubstituted aryl, mono-substituted aryl wherein the substituent is meta or para to the linking carbon, or substituted or unsubstituted heterocycle.

15. The composition of claim 13 wherein $R^2$ is unsubstituted phenyl; mono-substituted phenyl wherein the substituent is meta or para to the linking carbon and is halogen, $C_{1-6}$ alkyl, or $C_{1-6}$ alkoxy; or a five- or six-member heteroaryl having at least O or S.

16. The composition of claim 13 wherein $R^2$ is unsubstituted phenyl; mono-substituted phenyl with fluoro, chloro, or methyl, at a position meta or para to the linking carbon; thiophene-2-yl; or furan-2-yl.

17. The composition of claim 13 wherein each of $R^4$, $R^5$, $R^6$ and $R^7$ is the same or different and independently hydrogen, or halogen, or $C_{1-6}$ alkyl.

18. The composition of claim 13 wherein each of $R^4$, $R^5$, $R^6$ and $R^7$ is hydrogen.

19. The composition of claim 13 wherein $R^3$ is hydrogen, halogen, or $C_{1-6}$ alkyl.

20. The composition of claim 13 wherein $R^3$ is hydrogen, halogen, or methyl.

21. The composition of claim 13 wherein the compound is
2-(4-(4-bromophenylsulfonyl)-2-phenyloxazol-5-ylthio)acetamide,
2-(4-(4-chlorophenylsulfonyl)-2-phenyloxazol-5-ylthio)acetamide,
2-(2-phenyl-4-tosyloxazol-5-ylthio)acetamide,
2-(2-phenyl-4-(phenylsulfonyl)oxazol-5-ylthio)acetamide,
2-(2-(4-fluorophenyl)-4-tosyloxazol-5-ylthio)acetamide,
2-(4-(4-chlorophenylsulfonyl)-2-(4-fluorophenyl)oxazol-5-ylthio)acetamide,
2-(2-(4-fluorophenyl)-4-(4-fluorophenylsulfonyl)oxazol-5-ylthio)acetamide,
2-(2-(4-fluorophenyl)-4-(phenylsulfonyl)oxazol-5-ylthio)acetamide,
2-(4-(4-bromophenylsulfonyl)-2-p-tolyloxazol-5-ylthio)acetamide,
2-(2-p-tolyl-4-tosyloxazol-5-ylthio)acetamide,
2-(4-(4-chlorophenylsulfonyl)-2-p-tolyloxazol-5-ylthio)acetamide,
2-(4-(phenylsulfonyl)-2-p-tolyloxazol-5-ylthio)acetamide,
2-(4-(4-chlorophenylsulfonyl)-2-(thiophen-2-yl)oxazol-5-ylthio)acetamide,
2-(2-(thiophen-2-yl)-4-tosyloxazol-5-ylthio)acetamide,
2-(4-(4-fluorophenylsulfonyl)-2-(thiophen-2-yl)oxazol-5-ylthio)acetamide,
2-(4-(phenylsulfonyl)-2-(thiophen-2-yl)oxazol-5-ylthio)acetamide,
2-(4-(4-chlorophenylsulfonyl)-2-(furan-2-yl)oxazol-5-ylthio)acetamide,
2-(4-(4-bromophenylsulfonyl)-2-(furan-2-yl)oxazol-5-ylthio)acetamide, or
2-(2-(furan-2-yl)-4-tosyloxazol-5-ylthio)acetamide.

22. The composition of claim 11 wherein $R^1$ is S—N-(furan-2-yl-methyl)-2-mercaptoacetamidyl) and each of $R^4$, $R^5$, $R^6$ and $R^7$ is hydrogen and the compound has the following substructure of formula (Ic):

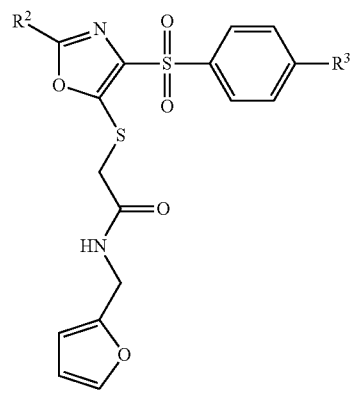

or a pharmaceutically acceptable salt, prodrug or stereoisomer thereof, wherein $R^3$ is hydrogen, halogen, or alkyl.

23. The composition of claim 11 wherein $R^3$ is hydrogen, halogen, or methyl.

24. The composition of claim 11 wherein $R^3$ is bromo or chloro.

25. The composition of claim 22 wherein $R^2$ is unsubstituted aryl; mono-substituted aryl wherein the substituent is meta or para to the linking carbon; or substituted or unsubstituted heterocycle.

26. The composition of claim 22 wherein $R^2$ is unsubstituted phenyl; or mono-substituted phenyl wherein the substituent is meta or para to the linking carbon and the substituent is halogen, $C_{1-6}$ alkyl, or $C_{1-6}$ alkoxy.

27. The composition of claim 22 wherein $R^2$ is unsubstituted phenyl.

28. The compound of claim 22 wherein the compound is 2-(4-(4-bromophenylsulfonyl)-2-phenyloxazol-5-ylthio)-N-(furan-2-ylmethyl)acetamide or 2-(4-(4-chlorophenylsulfonyl)-2-phenyloxazol-5-ylthio)-N-(furan-2-ylmethyl)acetamide.

29. The composition of claim 1 wherein $R^2$ is phenyl, 2-fluorophen-2-yl, 4-fluorophen-1-yl, 2-chlorophen-1-yl, 4-methylphen-1-yl, 2-methyoxyphen-1-yl, thiophene-2-yl, or furan-2-yl.

30. The composition of claim 1 wherein $R^3$ is hydrogen, fluoro, chloro, bromo or methyl.

31. The composition of claim 1 wherein X is NH.

32. A method for treating a disease or disorder associated with aberrant transport of urea in a subject by administering to the subject the composition according to claim 1.

33. The method of claim 32 wherein the disease or disorder is associated with a fluid retention imbalance.

34. The method according to claim 33 wherein the fluid retention imbalance comprises urea clearance insufficiency.

35. The method according to claim 34 wherein urea clearance insufficiency is renal urea clearance insufficiency.

36. The method of claim 32 wherein the disease or disorder is selected from a cardiovascular disease, syndrome of inappropriate antidiuretic hormone secretion (SIADH), cirrhosis, azotemia, acute renal failure, chronic renal insufficiency, fluid retention, and abnormal uresis.

37. The method of claim 36 wherein the cardiovascular disease or disorder is hypertension or congestive heart failure.

38. The method according to claim 32 wherein treating the disease or disorder comprises inhibiting transport of urea by at least one urea transporter.

39. The method according to claim 38 wherein the at least one urea transporter is a UT-B transporter.

40. The method according to claim 38 wherein the at least one urea transporter is a UT-A transporter selected from UT-A1, UT-A2, UT-A3, UT-A4, and UT-A5.

\* \* \* \* \*

UNITED STATES PATENT AND TRADEMARK OFFICE
CERTIFICATE OF CORRECTION

| | |
|---|---|
| PATENT NO. | : 8,394,788 B2 |
| APPLICATION NO. | : 12/515000 |
| DATED | : March 12, 2013 |
| INVENTOR(S) | : Alan S. Verkman et al. |

Page 1 of 1

It is certified that error appears in the above-identified patent and that said Letters Patent is hereby corrected as shown below:

In the Claims

Column 60, Line 45:
"23. The composition of claim 11 wherein $R^3$ is hydrogen," should read, --23. The composition of claim 22 wherein $R^3$ is hydrogen,--.

Column 60, Line 47:
"24. The composition of claim 11 wherein $R^3$ is bromo or" should read, --24. The composition of claim 22 wherein $R^3$ is bromo or--.

Signed and Sealed this
Twenty-fourth Day of March, 2015

Michelle K. Lee
*Director of the United States Patent and Trademark Office*